United States Patent
Lai et al.

(10) Patent No.: US 10,695,016 B2
(45) Date of Patent: Jun. 30, 2020

(54) HANDHELD RADIATION IMAGE DETECTING SYSTEM AND OPERATING METHOD THEREOF

(71) Applicants: HannsTouch Solution Incorporated, Tainan (TW); Energy Resources International Co., LTD., New Taipei (TW)

(72) Inventors: Chi-Kuang Lai, Tainan (TW); Hsu-Ho Wu, Tainan (TW); Wei-Hsuan Ho, Tainan (TW); Ching-Feng Tsai, Tainan (TW); Che-Yu Chuang, Tainan (TW); Tsung-Min Yang, New Taipei (TW); Yu-Wei Chen, New Taipei (TW)

(73) Assignees: HannsTouch Solution Incorporated, Tainan (TW); Energy Resources International Co., LTD., New Taipei (TW)

( * ) Notice: Subject to any disclaimer, the term of this patent is extended or adjusted under 35 U.S.C. 154(b) by 169 days.

(21) Appl. No.: 16/000,910

(22) Filed: Jun. 6, 2018

(65) Prior Publication Data
US 2019/0246996 A1 Aug. 15, 2019

(30) Foreign Application Priority Data

Feb. 13, 2018 (TW) .............................. 107105224 A

(51) Int. Cl.
| | | |
|---|---|---|
| *A61B 6/00* | (2006.01) | |
| *G01T 7/00* | (2006.01) | |
| *G01T 1/161* | (2006.01) | |
| *A61B 6/08* | (2006.01) | |

(52) U.S. Cl.
CPC .............. *A61B 6/4405* (2013.01); *A61B 6/08* (2013.01); *A61B 6/4452* (2013.01); *A61B 6/542* (2013.01); *A61B 6/547* (2013.01); *G01T 1/1611* (2013.01); *G01T 7/005* (2013.01)

(58) Field of Classification Search
CPC ...... A61B 6/4405; A61B 6/4494; G03B 42/04
See application file for complete search history.

(56) References Cited

U.S. PATENT DOCUMENTS

| | | | |
|---|---|---|---|
| 9,332,951 B2 * | 5/2016 | Inglese | ..................... A61B 6/08 |
| 2007/0046525 A1 * | 3/2007 | Holbrook | ................ G01S 13/89 342/22 |
| 2009/0060145 A1 * | 3/2009 | Tranchant | .............. A61B 6/145 378/207 |
| 2009/0257564 A1 * | 10/2009 | Kito | ..................... A61B 6/4283 378/206 |
| 2011/0079734 A1 * | 4/2011 | Grodzins | ............... G01N 21/63 250/461.1 |
| 2019/0209870 A1 * | 7/2019 | Ueno | .................... A61N 5/1067 |

* cited by examiner

*Primary Examiner* — Yara B Green
(74) *Attorney, Agent, or Firm* — Winston Hsu

(57) ABSTRACT

A handheld radiation image detecting system and an operation method thereof are provided. The handheld radiation image detecting system includes a handheld device including a radiation emitter and a first transceiver and a sensing device including a radiation image sensor and a second transceiver. The first transceiver is coupled to the radiation emitter and used for generating a first wave with directionality. The second transceiver is used for receiving the first wave and for generating a second wave with directionality, and the first transceiver is used for receiving the second wave.

18 Claims, 21 Drawing Sheets

HANDHELD RADIATION IMAGE DETECTING SYSTEM AND OPERATING METHOD THEREOF

CROSS REFERENCE TO RELATED APPLICATION

The present application claims the priority benefit of Taiwan patent application serial no. 107105224, filed Feb. 13, 2018. The entirety of the above-mentioned patent application is hereby incorporated by reference herein.

BACKGROUND OF THE INVENTION

1. Field of the Invention

The present invention relates to a handheld radiation image detecting system and an operating method thereof.

2. Description of the Prior Art

Conventional digital X-ray photography can be divided into a stationary type and a portable type. Most of digital X-ray photography equipment recently is stationary type. For this reason, an examinee needs to go to a specific place, such as hospital, to be inspected, which causes inconvenience of the examinee, and also results in that patient cannot be inspected at the position required by the patient. Although a portable X-ray photography equipment has been developed, the relative position between X-ray emitter and X-ray sensor or the relative angle between the X-ray emitter and the X-ray sensor are not stable, so it is not easy to simply, quickly and accurately maintain the relative position between the X-ray emitter and the X-ray sensor in a perpendicular direction. Especially, handheld X-ray emitter is not fixed on the mechanism, and if there is no safe automatic activating system, X ray may be emitted when the X-ray emitter is disposed at incorrect position or incorrect angle. Thus, the examinee will receive unnecessary dose of radiation, and the examinee may be harmed by the radiation.

SUMMARY OF THE INVENTION

In accordance with an embodiment of the present invention, a handheld radiation image detecting system is provided for inspecting an examinee. The handheld radiation image detecting system includes a handheld device and a sensing device. The handheld device includes a radiation emitter and a first transceiver, in which the first transceiver is coupled to the radiation emitter, the first transceiver includes a first emitter and a first receiver, and the first emitter is used for generating a first wave with directionality. The sensing device includes a radiation image sensor and at least one second transceiver, in which the at least one second transceiver includes a second emitter and a second receiver, the second receiver is used for receiving the first wave, the second emitter is used for generating a second wave with directionality, and the first receiver is used for receiving the second wave.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
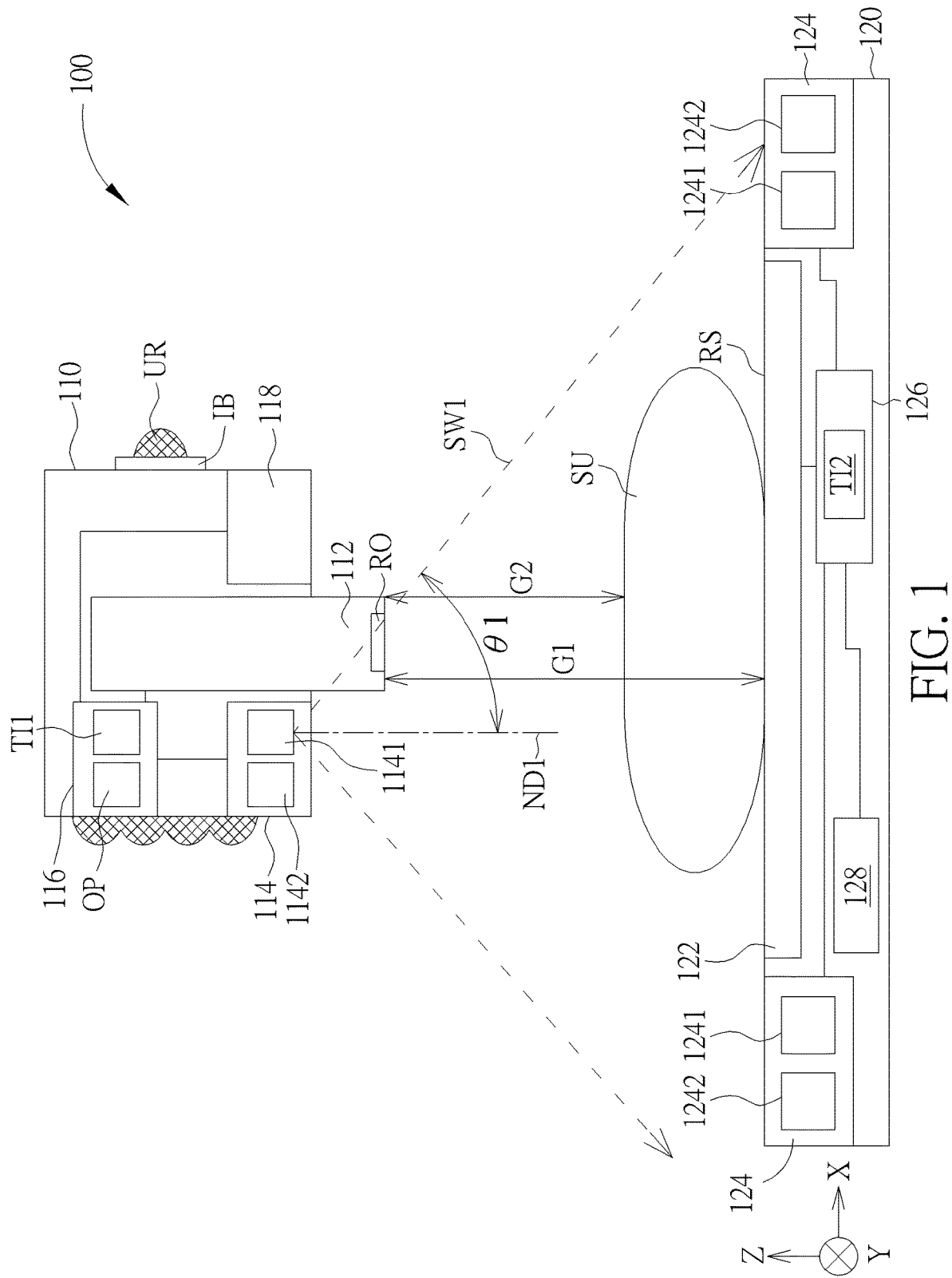
FIG. 1 schematically illustrates a side view of a handheld radiation image detecting system according to a first embodiment of the present invention.

To provide a better understanding of the present invention, embodiments accompanied with drawings are detailed as follows. For explanation, the components shown in the drawings of the present invention are not drawn to scale, and the numbers and dimensions of the components are only for illustration and not for limiting the scope of the present invention.

Figure 2:
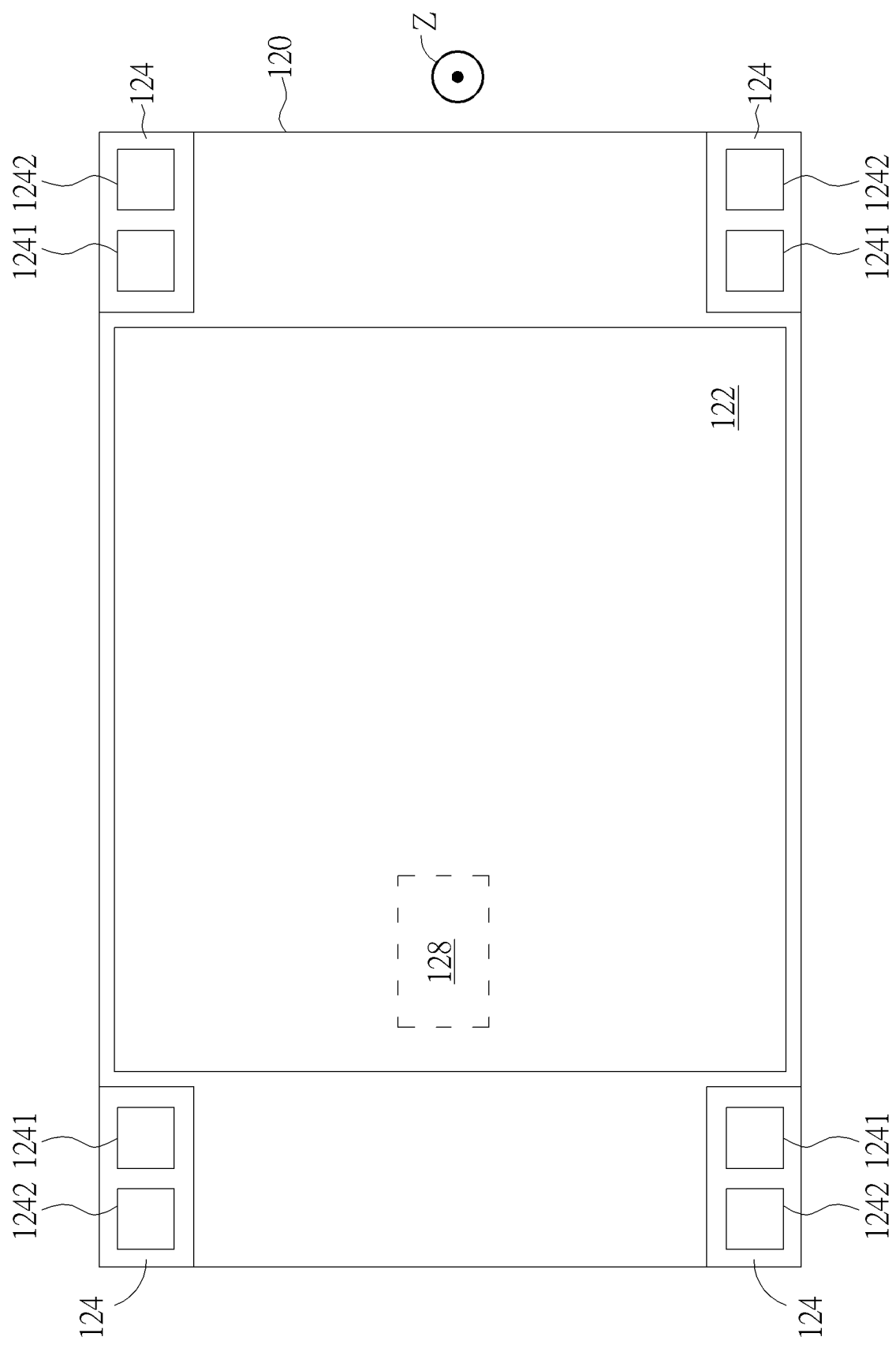
FIG. 2 schematically illustrates a sensing device according to the first embodiment of the present invention.

FIG. 1 schematically illustrates a side view of a handheld radiation image detecting system according to a first embodiment of the present invention, and FIG. 2 schematically illustrates a sensing device according to the first embodiment of the present invention. As shown in FIG. 1, the handheld radiation image detecting system 100 of this embodiment is adapted for inspecting an anatomy of a part of an examinee SU, such as an organ structure or a bone structure. The handheld radiation image detecting system 100 may include a handheld device 110 and a sensing device 120. The handheld device 110 is used for generating a radiation for inspecting, and the sensing device 120 is used for detecting dose of the radiation penetrating through the examinee SU, so as to generate an image information. Specifically, the handheld device 110 has a radiation outlet RO for emitting the radiation. The sensing device 120 has a radiation receiving surface RS for allowing the radiation entering. During inspecting, the radiation outlet RO is disposed to face the radiation receiving surface RS, and the examinee SU is located between the radiation outlet RO and the radiation receiving surface RS and in tight contact with the sensing device 120. For example, the examinee SU may be lay on the radiation receiving surface RS with the examinee's back or side, or the examinee stands while his back is in tight contact with the radiation receiving surface RS, but the present invention is not limited thereto. The radiation of this embodiment is for instance X ray, but not limited thereto. It is noted that the handheld device 110 allows a user UR, such as a radiologist, to hold with a hand, so that a relative position between the radiation outlet RO and the radiation receiving surface RS may be controlled by the hand. In another embodiment, the handheld device 110 may include a grip, so that the user UR may control a direction that the radiation outlet RO faces by holding the grip.

The handheld device and the sensing device of the present invention may transmit signals to each other with a wireless communication method. In this embodiment, the handheld device 110 may include a radiation emitter 112 and a first transceiver 114. The radiation emitter 112 is used for generating the radiation, and the first transceiver 114 is coupled to the radiation emitter 112. Specifically, the handheld device 110 may include a first control component 116 coupled between the first transceiver 114 and the radiation emitter 112 and used for controlling the signal transmission between the first transceiver 114 and the radiation emitter 112. The first transceiver 114 includes a first emitter 1141 and a first receiver 1142. The first emitter 1141 may be used for generating a first wave SW1 with directionality. The type of the first wave SW1 may be for example an infrared light, a visible light or an ultrasonic wave.

The sensing device 120 may include a radiation image sensor 122 and at least one second transceiver 124. The radiation image sensor 122 is used for detecting the dose of the radiation penetrating through a part of the examinee SU. For instance, the radiation image sensor 122 may be a panel detector including a radiation converting layer, a plurality of sensing units arranged in an array and an array circuit (not shown in figures). The radiation converting layer covers the sensing units and is used for absorbing the radiation and converting the radiation into visible light or light that the sensing units can absorb. The radiation converting layer may be for example an inorganic scintillator, in which the material of the scintillator may include, but not limited thereto, cesium iodide or gadolinium oxysulfide. The sensing units may include for example photodiodes for converting the light generated from the radiation converting layer into electric charges, and the sensing units may correspond to the pixels of the image information respectively. The array circuit may include a plurality of thin-film transistors, a plurality of gate lines, a plurality of bias lines and a plurality of data lines. Each thin-film transistor is electrically connected to a corresponding one of the sensing units, and the thin-film transistors may be turned on to measure the electric charges of the pixels by signals of the gate lines, the data lines and the bias lines. The sensing units and the array circuit may be manufactured for example by the processes for forming the array substrate of the display device. The radiation image sensor 122 of the present invention is not limited to the mentioned above, and it is understood to the person skilled in the art that the radiation image sensor 122 may further include a collimator disposed on the radiation converting layer and used for facilitating the radiation that penetrates through the examinee to correspondingly enter the radiation converting layer and preventing the scattering of the radiation from affecting the accuracy of the detected image.

The second transceiver 124 is coupled to the radiation image sensor 122 and used for receiving the first wave SW1 and generating a second wave SW2 with directionality, and the first transceiver 114 may receive the second wave SW2, so that the handheld device 110 and the sensing device 120 may achieve signal transmission in the way of wireless communication through the first transceiver 114 and the second transceiver 124. Since that, the radiation emitter 112 and the radiation image sensor 122 can both be ready to perform the radiation inspection at time points close to each other, so as to clearly inspect an image of the radiation and also reduce inspecting time. The second transceiver 124 may be disposed at a corner of the sensing device 120 to facilitate the second transceiver 124 to detect the first wave SW1 with directionality when the first wave SW1 cannot penetrate through the human body. Preferably, when the examinee SU is lay on the sensing device 120, the second transceiver 124 may not be shielded by the examinee SU, but not limited thereto. Specifically, the sensing device 120 may include a second control component 126 coupled to the second transceiver 124 and the radiation image sensor 122 and used for controlling the signal transmission between the second transceiver 124 and the radiation image sensor 122. The second transceiver 124 includes a second emitter 1241 and a second receiver 1242, in which the second receiver 1242 is used for receiving the first wave SW1, the second emitter 1241 is used for generating the second wave SW2, and the first receiver 1142 may be used for receiving the second wave SW2. In other words, the second receiver 1242 is designed to correspond to the first emitter 1141, and the first receiver 1142 is designed to correspond to the second emitter 1242. The type of the second wave SW2 may be the same as or different from the type of the first wave SW1. For example, the first wave SW1 and the second wave SW2 may be an infrared light, a visible light or an ultrasonic wave. When the type of the first wave SW1 is identical to the type of the second wave SW2, the modulation code of the first wave SW1 may be different from the modulation code of the second wave SW2, so as to avoid interfering with each other. In this embodiment, the first control component 116 and the second control component 126 may control the signal transmission between the first transceiver 114 and the second transceiver 124.

Figure 3:
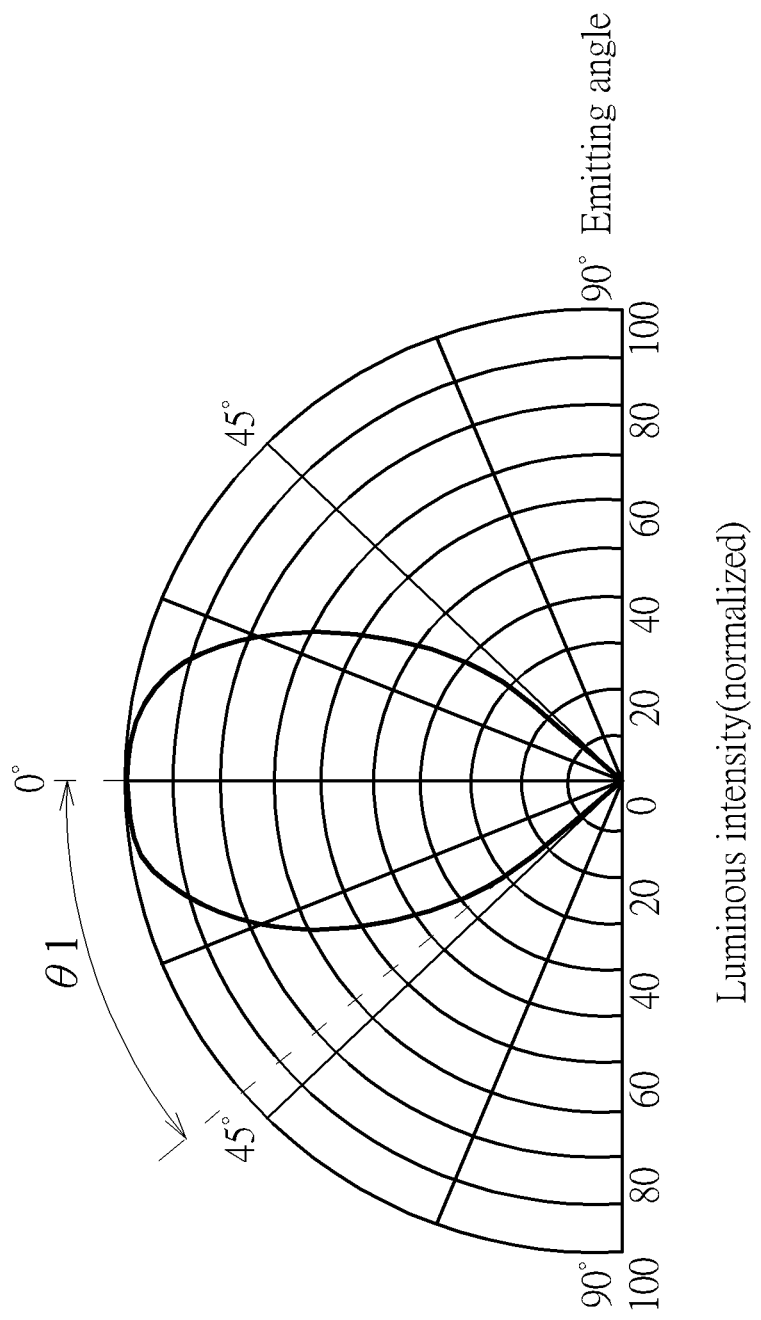
FIG. 3 schematically illustrates a relation between a luminous intensity and an emitting angle of the first wave according to the first embodiment of the present invention.

In this embodiment, the sensing device 120 may include at least two second transceivers 124 disposed respectively at two corners of the sensing device 120 opposite to each other in a top view direction Z perpendicular to the radiation receiving surface RS and coupled to the second control component 126. The radiation receiving surface RS may be for example located in a XY plane formed by horizontal directions X, Y. Since the first emitter 1141 emits the first wave SW1 with a specific beam angle θ1, through disposing the second transceivers 124 at the two opposite corners of the sensing device 120, the second transceivers 124 can be used for detecting whether the radiation outlet RO aims at the radiation receiving surface RS. For example, as shown in FIG. 2, the sensing device 120 may include four second transceivers 124 disposed at four corners of the sensing device 120 respectively. Also, the first emitter 1141 and the radiation outlet RO shown in FIG. 1 are preferably located on surfaces of the handheld device 110 facing the same direction, but not limited thereto. Hence, when the second transceivers 124 are located in the irradiation range of the first wave SW1, the handheld radiation image detecting system 100 can judge that the radiation outlet RO of the handheld device 110 aims at the radiation receiving surface RS of the sensing device 120. For example, the method for judging that the radiation outlet RO aims at the radiation receiving surface RS may be performed by comparing signal values of the first wave SW1 received by the second transceivers 124 with each other, which means when each signal value is greater than a pre-determined value, and a difference between any two of the signal values is less than a specific value, it can be judged that the handheld device 110 aims at the sensing device 120. Thus, in this embodiment, through the beam angle θ1 of the first emitter 1141 and the disposition of the second transceivers 124, the handheld radiation image detecting system 100 may not only limit an angle included between a center axis of the radiation outlet RO and a normal direction of the radiation receiving surface RS to be in a certain range, but also confine a spacing between the center axis of the radiation outlet RO and a center of the sensing device 120 in a horizontal plane (the XY plane) to be in a certain range. Besides, since the beam angle θ1 of the first emitter 1141 may be designed to be in a specific range, the spacing between the handheld device 110 and the sensing device 120 in the top view direction Z may be confined to be greater than a specific distance on condition that all of the second transceivers 124 receive the first wave SW1 or each signal value of the received first wave SW1 comply with the pre-determined value. For example, revert to FIG. 3, which schematically illustrates a relation between a luminous intensity and an emitting angle of the first wave according to the first embodiment of the present invention. As shown in FIG. 3, the beam angle θ1 of the first emitter 1141 of this embodiment is defined as an angle included between a normal direction ND1 of the emitting surface of the first emitter 1141 (that is 0 degree) and a propagation direction of light with largest scattering angle. In this embodiment, when the first wave SW1 is a light wave, the beam angle θ1 of the first emitter 1141 may be for example less than 45 degree, but the present invention is not limited thereto. Additionally, each second emitter 1241 of this embodiment may generate one second wave SW2 with directionality, which means the second wave SW2 may have another beam angle, so that the first receiver 1142 can be further limited to be located in the irradiation range of each second wave SW2 to judge that the handheld device 110 aims at the sensing device 120. Thus, the angle included between the center axis of the radiation outlet RO and the normal direction of the radiation receiving surface RS may be further confined to avoid the inclined angle of the handheld device 110 relative to the radiation receiving surface RS being over large.

In this embodiment, the handheld device 110 may further include a third emitter 118 and a first timer TI1, and the sensing device 120 may further include a third receiver 128 and a second timer TI2. The third emitter 118 is coupled to the first control component 116, the first timer TI1 is disposed in the first control component 116, the third receiver 128 is coupled to the second control component 126, and the second timer TI2 may be disposed in the second control component 126, but not limited thereto. In another embodiment, the first timer TI1 may be located outside the first control component 116. The second timer TI2 may be disposed outside the second control component 126 and coupled to the second control component 126. In this embodiment, the third emitter 118, the third receiver 128, the first timer TI1 and the second timer TI2 may be used for detecting a spacing between the handheld device 110 and the sensing device 120. Specifically, the third emitter 118 is coupled to the first transceiver 114 and the first timer TI1 separately through the first control component 116 and used for generate the third wave SW3. The third receiver 128 is coupled to at least one second transceiver 124 and the second timer TI2 through the second control component 126 and used for receiving the third wave SW3, and the first timer TI1 and the second timer TI2 are used for counting the propagaiong time of the third wave SW3. A propagation speed of the third wave SW3 is less than a propagation speed of the first wave SW1 and a propagation speed of the second wave SW2, preferably far less than the propagation speed of the first wave SW1 and the propagation speed of the second wave SW2. For example, the third wave SW3 may be an ultrasonic wave that has the propagation speed of about 340 m/s, and the first wave SW1 and the second wave SW2 may include a infrared light or a visible light that has the propagation speed of about $3 \times 10^8$ m/s. The method for measuring the spacing between the handheld device 110 and the sensing device 120 through the third emitter 118, the third receiver 128, the first timer TI1 and the second timer TI2 is detailed in the following description. The handheld radiation image detecting system 100 may further include a calculator OP disposed in the handheld device 110 or the sensing device 120 and used for calculating the spacing between the handheld device 110 and the sensing device 120 according to the propagation time and the propagation speed of the third wave SW3. For instance, the calculator OP may be disposed in the first control component 116, but not limited thereto.

Figure 4:
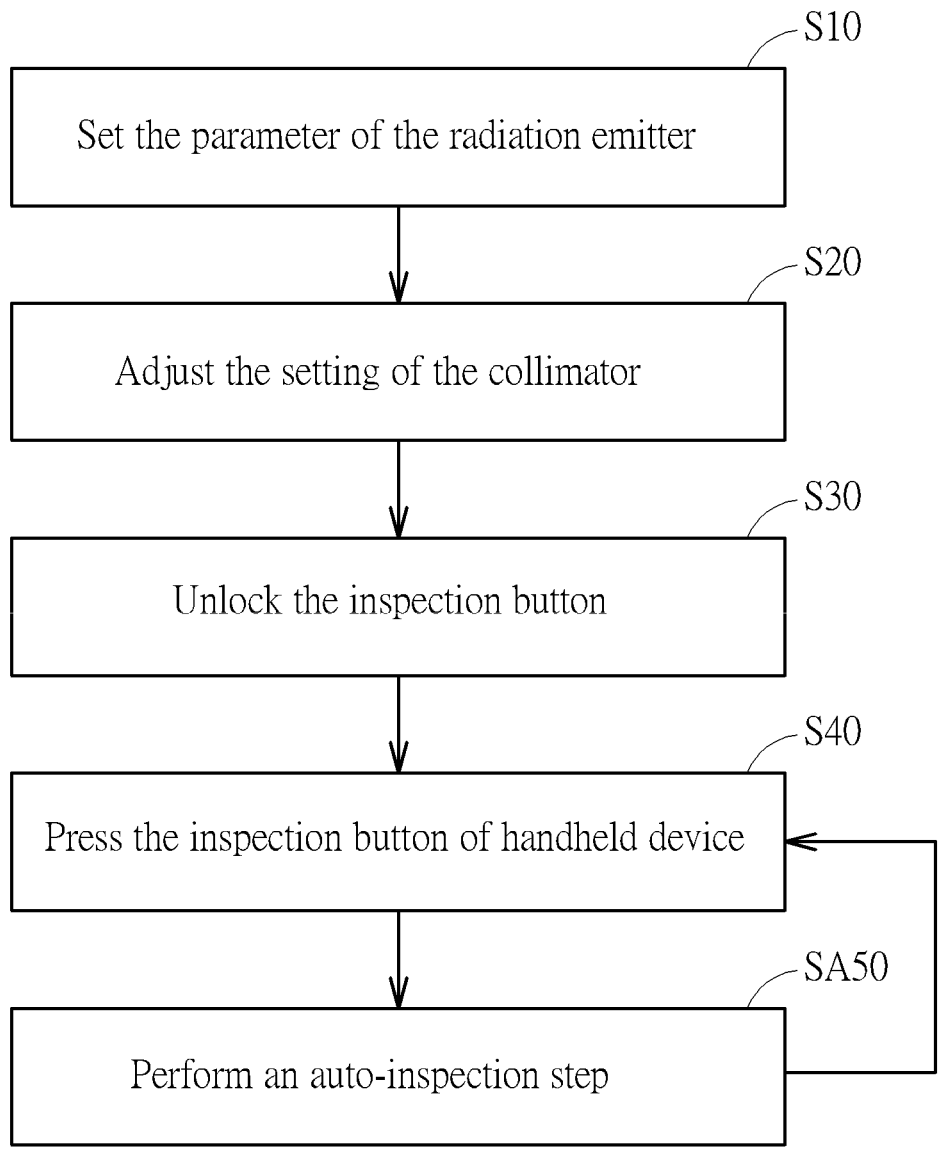
FIG. 4 schematically illustrates a flowchart of the operating method of the handheld radiation image detecting system according to the first embodiment of the present invention.

The operating method of the handheld radiation image detecting system 100 of this embodiment is further detailed in the following description. Refer to FIG. 4, which schematically illustrates a flowchart of the operating method of the handheld radiation image detecting system according to the first embodiment of the present invention. As shown in FIG. 4, the operating method of the handheld radiation image detecting system 100 provided in this embodiment may include sequentially performing following step S10 to auto-inspection step SA50. In step S40, as shown in FIG. 1, the user UR may press the inspection button IB of the handheld device 110 to activate the auto-inspection step SA50 of the handheld radiation detecting system 100. Since after activating the auto-inspection step SA50, the user UR doesn't need to press any button, i.e. the handheld radiation image detecting system 100 continues proceeding until the pre-determined condition is not complied or the image information is generated, the examinee SU is in tight contact with the radiation receiving surface RS before the step S40. Also, the operating time from pressing the inspection button IB to finishing inspection by the handheld radiation image detecting system 100 is extremely short, so the hand of the user UR doesn't need to be fixed at the same position too long, and the operating time may be for example less than about 500 ms. In this embodiment, before the step S40 of pressing the inspection button IB, the operating method of the handheld radiation image detecting system 100 may further include a step of setting a parameter by the user UR. For example, the step of setting the parameter may include the step S10 and step S20, but not limited thereto. In the step S10, the user UR set the parameter of the radiation emitter 112, for example the exposure time of the radiation emitter 112 is set to adjust the dose of the radiation according to the part of the examinee SU to be inspected or the situation of the examinee SU. In the step S20, the user UR may adjust the setting of the collimator. The parameter of the present invention is not limited to the mentioned above. For avoiding the radiation irradiating while accidentally pressing the inspection button IB, the operating method may further include the step S30 of unlocking the inspection button IB between setting the parameter and the step S40 of pressing the inspection button IB, so that the radiation emitter 112 can enter a ready state. For example, the step S30 of unlocking the inspection button IB may include identifying fingerprint of the user UR by a fingerprint sensor and judging whether the detected fingerprint is the same as a preset fingerprint. When the detected fingerprint is the same as the preset fingerprint, the step S30 is completed. When the detected fingerprint is not the same as the preset fingerprint, the radiation emitter 112 cannot enter the ready state, which means the auto-inspection step SA50 cannot be entered even though the inspection button IB is pressed. The examinee SU may be tightly located on the radiation receiving surface RS before setting the parameter or between setting the parameter and unlocking the inspection button IB.

Figure 5:
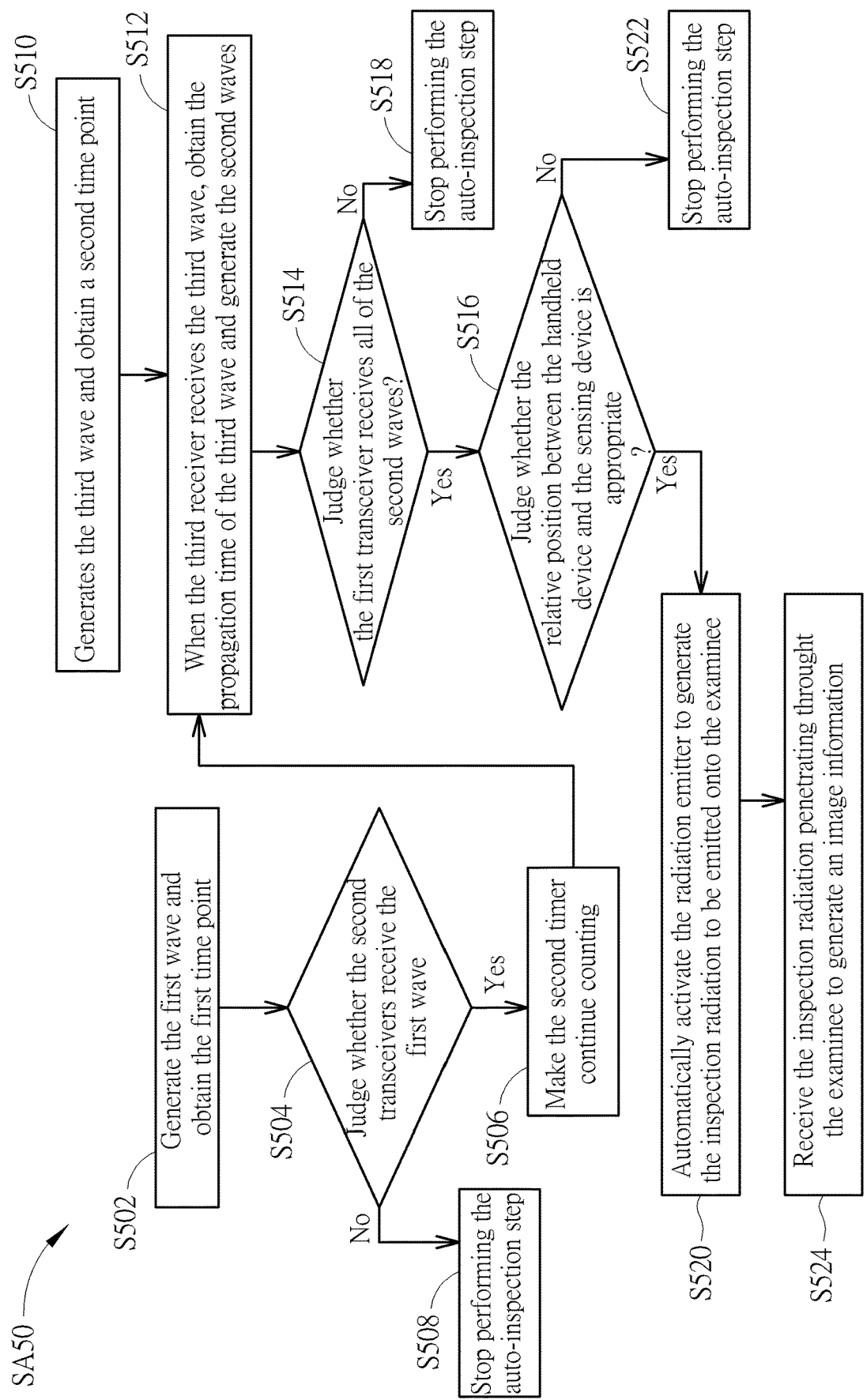
FIG. 5 schematically illustrates a flowchart of the auto-inspection step according to the first embodiment of the present invention.
Figure 6:
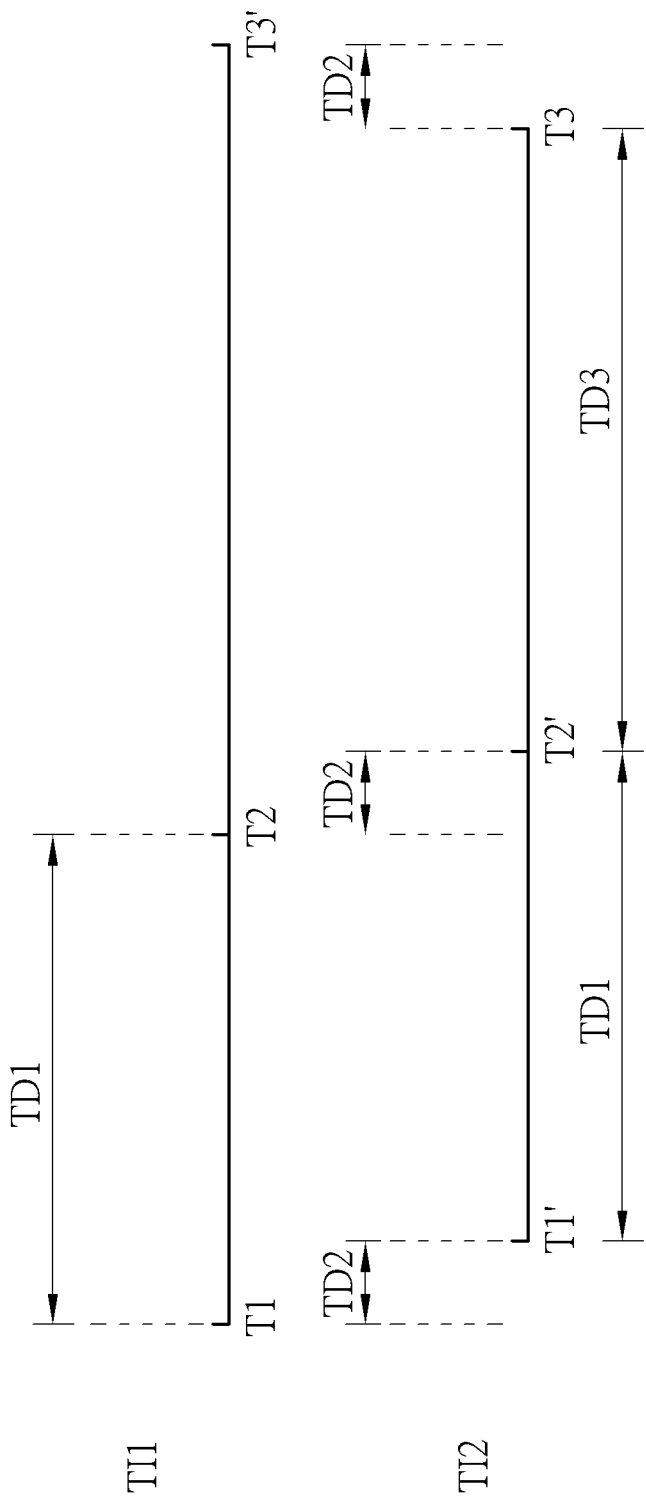
FIG. 6 illustrates a timing sequence of time points obtained by the first timer and the second timer according to the first embodiment of the present invention.
Figure 7:
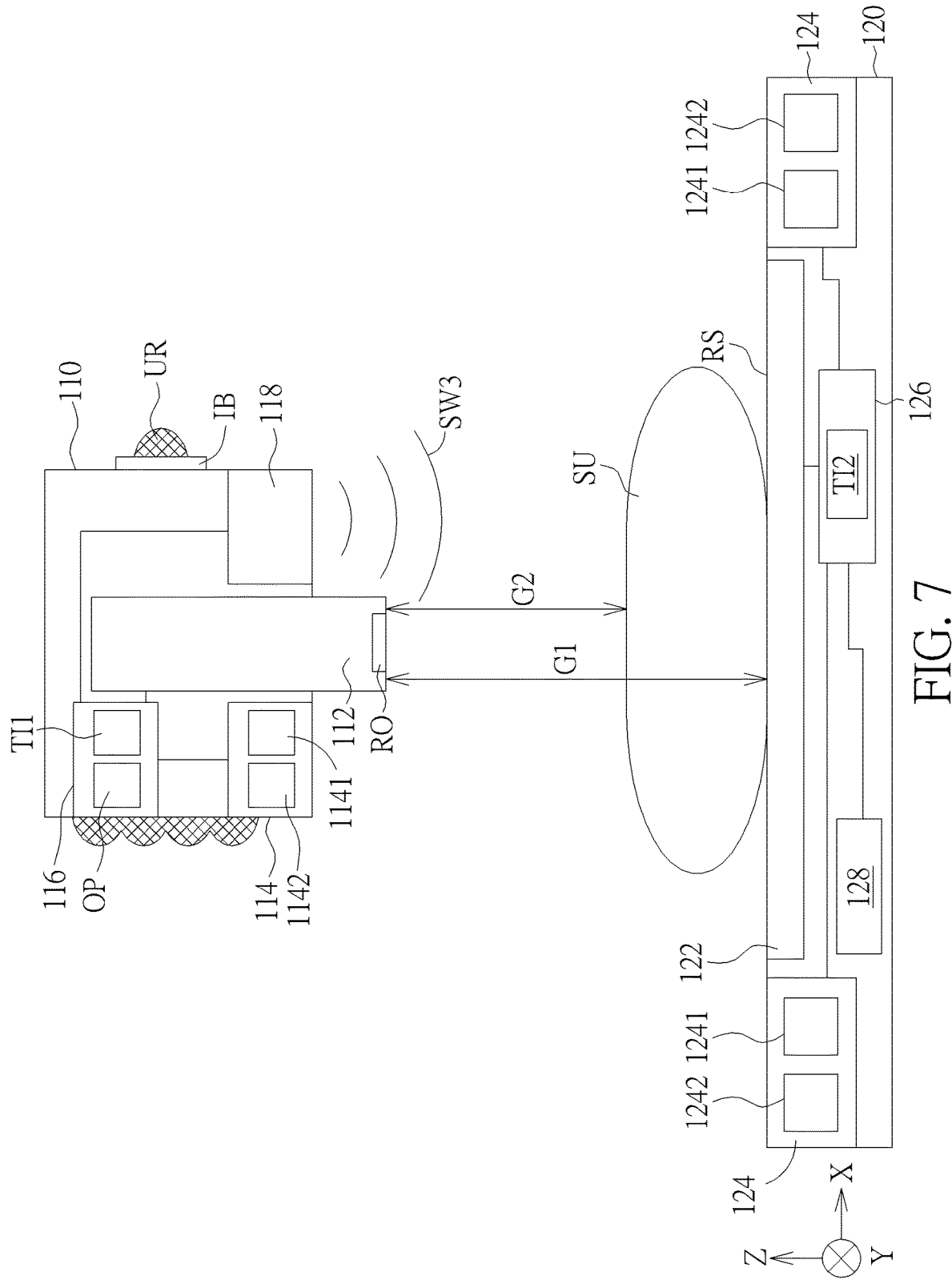
FIG. 7 schematically illustrates the third emitter generating the third wave according to the first embodiment of the present invention.
Figure 8:
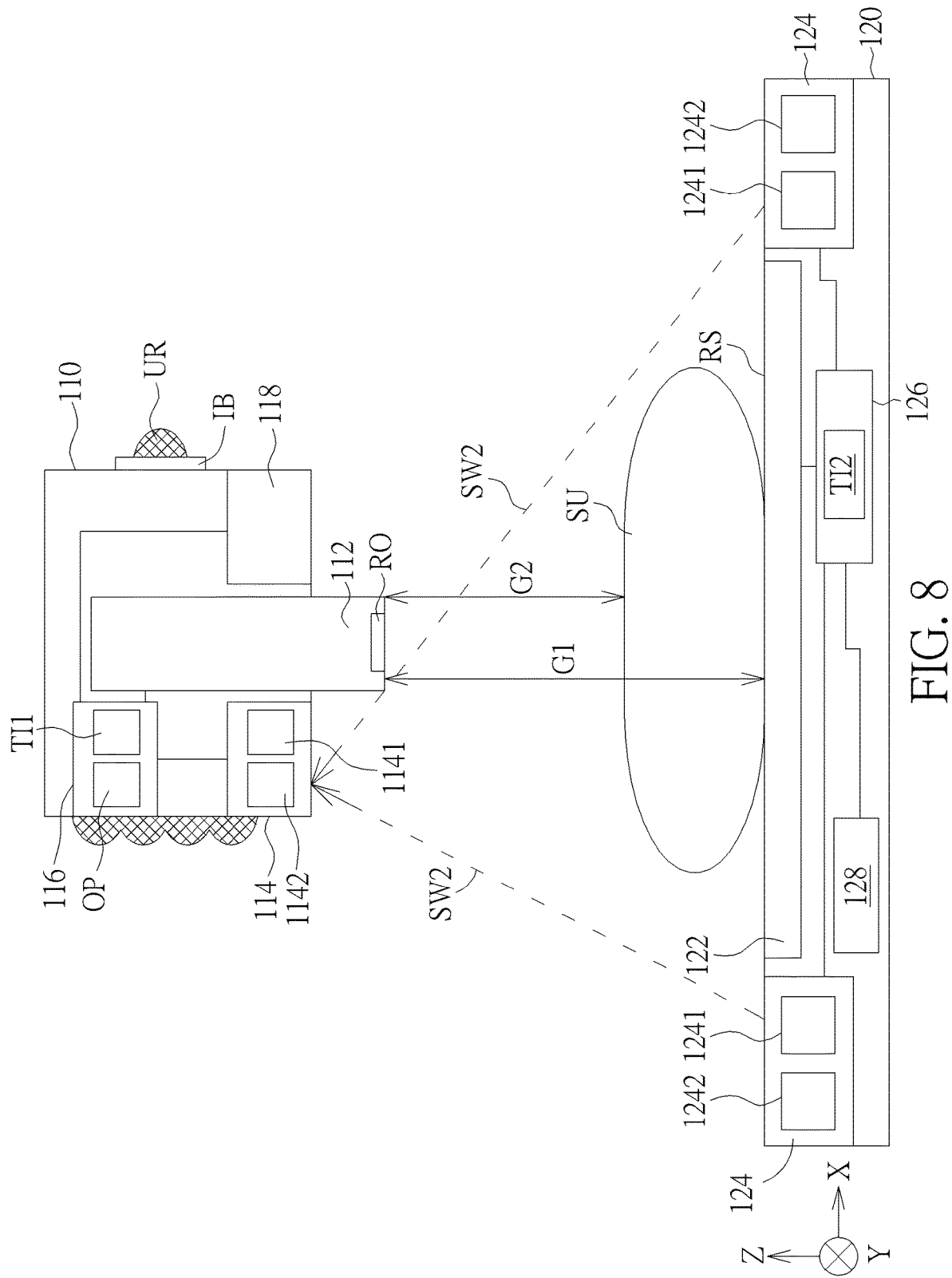
FIG. 8 schematically illustrates the second emitter generating the second wave according to the first embodiment of the present invention.
Figure 9:
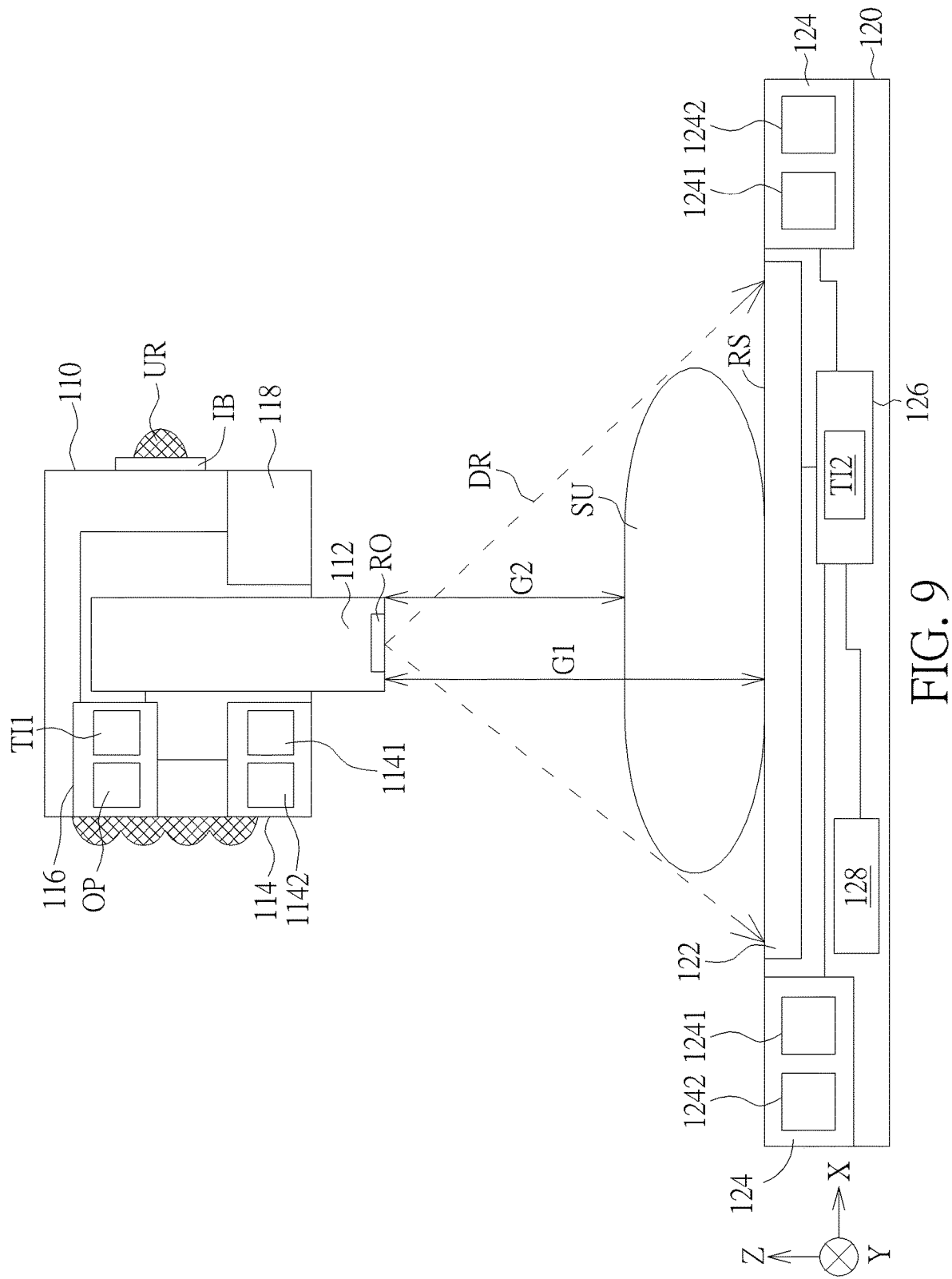
FIG. 9 schematically illustrates the radiation emitter generating the inspection radiation.

FIG. 5 schematically illustrates a flowchart of the auto-inspection step according to the first embodiment of the present invention, FIG. 6 illustrates a timing sequence of time points obtained by the first timer and the second timer according to the first embodiment of the present invention, FIG. 7 schematically illustrates the third emitter generating the third wave, FIG. 8 schematically illustrates the second emitter generating the second wave, and FIG. 9 schematically illustrates the radiation emitter generating an inspection radiation. As shown in FIG. 5, after the step S40 of pressing the inspection button IB, the auto-inspection step SA50 including sequentially performing step S502 to step S522 is performed and is detailed in the following description. As shown in FIG. 1 and FIG. 6, in the step S502, the first emitter 1141 generates the first wave SW1 with a first signal, and the first timer TI1 obtains a first time point T1 of generating the first wave SW1. Thereafter, in step S504, when the second receivers 1242 receive the first wave SW1, the second timer TI2 obtains another first time point T1' of receiving the first wave SW1 by the second receivers 1242. A second time difference exists between the first time points T1 and T1' and is substantially identical to the propagation time of the first wave SW1 from the first emitter 1141 to the second receivers 1242. In the step S504, the second control components 126 may further judge whether the second receiver 1242 of each second transceiver 124 receive the first wave SW1 or not, so that whether the radiation outlet RO substantially aims at the radiation receiving surface RS can be judged. Accordingly, whether the relative position between the handheld device 110 and the sensing device 120 in the horizontal plane (the XY plane) is appropriate can be judged. When all of the second receivers 1242 are judged to receive the first wave SW1, step S506 is performed to make the second timer TI2 continue counting. If one of the second receivers 1242 doesn't receive the first wave SW1, the second control component 126 performs step S508 to stop the auto-inspection step SA50. The condition for judging that the second receivers 1242 receive the first wave SW1 may be for example that the second receivers 124 receive the first wave SW1 or the signal values of the received first wave SW1 are greater than a pre-determined value, but not limited thereto.

As shown in FIG. 7, in step S510, the third emitter 118 generates the third wave SW3 to be emitted toward the sensing device 120, and the first timer TI1 obtain a second time point T2 of generating the third wave SW3. In this embodiment, the second time point T2 is later than the first time point T1 of generating the first wave SW1, and a first time difference TD1 exists between the first time point T1 and the second time point T2.

Subsequently, step S512 is performed to obtain the propagation time of the third wave SW3 by the second timer TI2 and to generate the second waves SW2 with second signals to be emitted toward the first transceiver 114 respectively by the second emitters 1241 when the second timer TI2 continues counting, as shown in FIG. 8. Specifically, when the third receiver 128 receives the third wave SW3, the third time point T3 of receiving the third wave SW3 by the third receiver 128, which is a time point of the third wave SW3 reaching the third receiver 128, can be obtained by the second timer TI2. In this embodiment, the first time difference TD1 is a pre-determined value that is prestored in the first control component 116, and the second component 126 may also prestore the pre-determined first time difference TD1, such that the second timer TI2 may start to count at the first time point T1' of receiving the first wave SW1 and set another second time point T2' until the first time difference TD1 passes. The another second time point T2' is regarded as a time point of starting to count when the third wave SW3 is generated; that is, a time difference between the first time point T1' and the second time point T2' of the second timer TI2 is also the first time difference TD1. Thus, the propagation time of the third wave SW3 may be obtained by counting a third time difference TD3 between the third time point T3 and the second time point T2'. It should be noted that through presetting the same first time difference TD1 in the first control component 116 and the second control component 126, the second time point T2' of the second timer TI2 starting to count when the third wave SW3 is generated is close to the second time point T2 of actually generating the third wave SW3, and a time difference between the second time points T2 and T2' is substantially the second time difference TD2. Since the propagation speed of the first wave SW1 is faster than the propagation speed of the third wave SW3, the propagation time of the first wave SW1 from first emitter 1141 to the second receiver 1242 (the second time difference TD2) can be ignored as compared with the propagation time of the third wave SW3 (the third difference TD3), such that the propagation time of the third wave SW3 is not affected by the signal transmission time between the first transceiver 114 and the second transceiver 124. In this embodiment, the first time difference TD1 is greater than the second time difference TD2 between the first time points T1 and T1'. In another embodiment, the first time point T1 of generating the first wave SW1 may be the same as the second time point T2 of generating the third wave SW3, which means the first time difference TD1 may be zero. In such situation, the propagation time of the third wave SW3 is the third time difference TD3 between the third time point T3 and the first time point T1'. In addition, in this embodiment, when the second control component 126 judges that the auto-inspection step is stopped, the second control component 126 cannot obtain the third time point through the second timer TI2, so that the second wave SW2 will not be generated. Also, the second signal of the second wave SW2 may include the information of the propagation time of the third wave SW3. For example, the second signal may include the information of the third time point T3 of the third wave SW3 reaching the third receiver 128 or the third time difference TD3 counted by the second control component 126.

Then, when the first receiver 1142 receives the second wave SW2, step S514 is performed to obtain another third time point T3' of receiving the third wave SW3 by the first timer TI1, so that the first control component 116 can obtain the time point when the third receiver 128 receives the third wave SW3. Accordingly, the first control component 116 may further confirm whether the time difference between the second time point T2 and the third time point T3' is close to the third time difference TD3. Also, in the step S514, the first control component 116 may judge whether the first receiver 1142 of the first transceiver 114 receives all of the second waves SW2 generated from the second emitter 1241, so that whether the handheld device 110 aims at the sensing device 120 can be effectively confirmed. When the first control component 116 judges that the first receiver 1142 receives all of the second waves SW2, step S516 is performed. If the first receiver 1142 doesn't receive one of the second waves SW2, the first control component 116 performs step S518 to stop the auto-inspection step SA50. The condition of judging that the first receiver 1142 receives all of the second wave SW2 can be for example the second waves SW2 are received or signal values of the received second waves SW2 are all greater than a pre-determined value, but is not limited thereto.

Thereafter, in the step S516, the first control component 116 may calculate the spacing G1 between the handheld device 110 and the sensing device 120 and judge whether the relative position between the handheld device 110 and the sensing device 120 is appropriate. Specifically, the calculator OP in the first control component 116 may obtain the propagation time of the third wave SW3 through the third time point T3' and the second time point T2 or the second signal and may calculate the spacing G1 between the radiation emitter 112 and the radiation image sensor 122 by an algorithm according to the propagation time and propagation speed of the third wave SW3, the position of the third emitter 118 in the handheld device 110 and the position of the third receiver 128 in the sensing device 120, so as to judge whether the relative position between the handheld device 110 and the sensing device 120 is appropriate. Moreover, after the spacing G1 (the distance in the top view direction Z) between the handheld device 110 and the sensing device 120 is calculated, whether the spacing G1 is greater than or equal to a pre-determined value or not can be judged, so as to further judge whether to generate an inspection radiation DR. For example, a spacing G2 between the radiation outlet RO of the radiation emitter 112 and the examinee SU must not be less 30 centimeter in medical standard, so the pre-determined value may be a sum of the spacing G2 and the thickness of the examinee SU, but the present invention is not limited thereto. According to the information of the examinee SU prestored in the handheld device 110, the first control component 116 can judge whether the spacing G1 is greater than or equal to the pre-determined value or not. When the spacing G1 is greater than or equal to the pre-determined value, the relative position between the handheld device 110 and the sensing device 120 is judged to be appropriate, and the step S520 is then preformed. If the spacing G1 is less than the pre-determined value, the step S522 is performed to stop the auto-inspection step SA50.

As shown in FIG. 9, in the step S520, when the relative position between the handheld device 110 and the sensing device 120 is appropriate, the radiation emitter 112 is automatically activated to generate the inspection radiation DR to be emitted onto the examinee SU. The step S524 is later performed, and the radiation image sensor 122 receives the inspection radiation DR penetrating throughout the examinee SU to generate an image information. Then, the image information can be displayed in the display device on the handheld device 110 or transferred to other device, such that the image information of the examinee SU can be inspected in real time. If the auto-inspection step SA50 is stopped, the display device may display a stopping information, so that the user UR may perform another inspection again from the step S40 after adjusting position by the hand.

The handheld radiation image detecting system and the operating method thereof of the present invention are not limited to the above-mentioned embodiment. The following description continues to detail the other embodiments or variant embodiments, and in order to simplify and show the difference between the other embodiments or variant embodiments and the above-mentioned embodiment, the same numerals denote the same components in the following description, and the same parts are not detailed redundantly.

Figure 10:
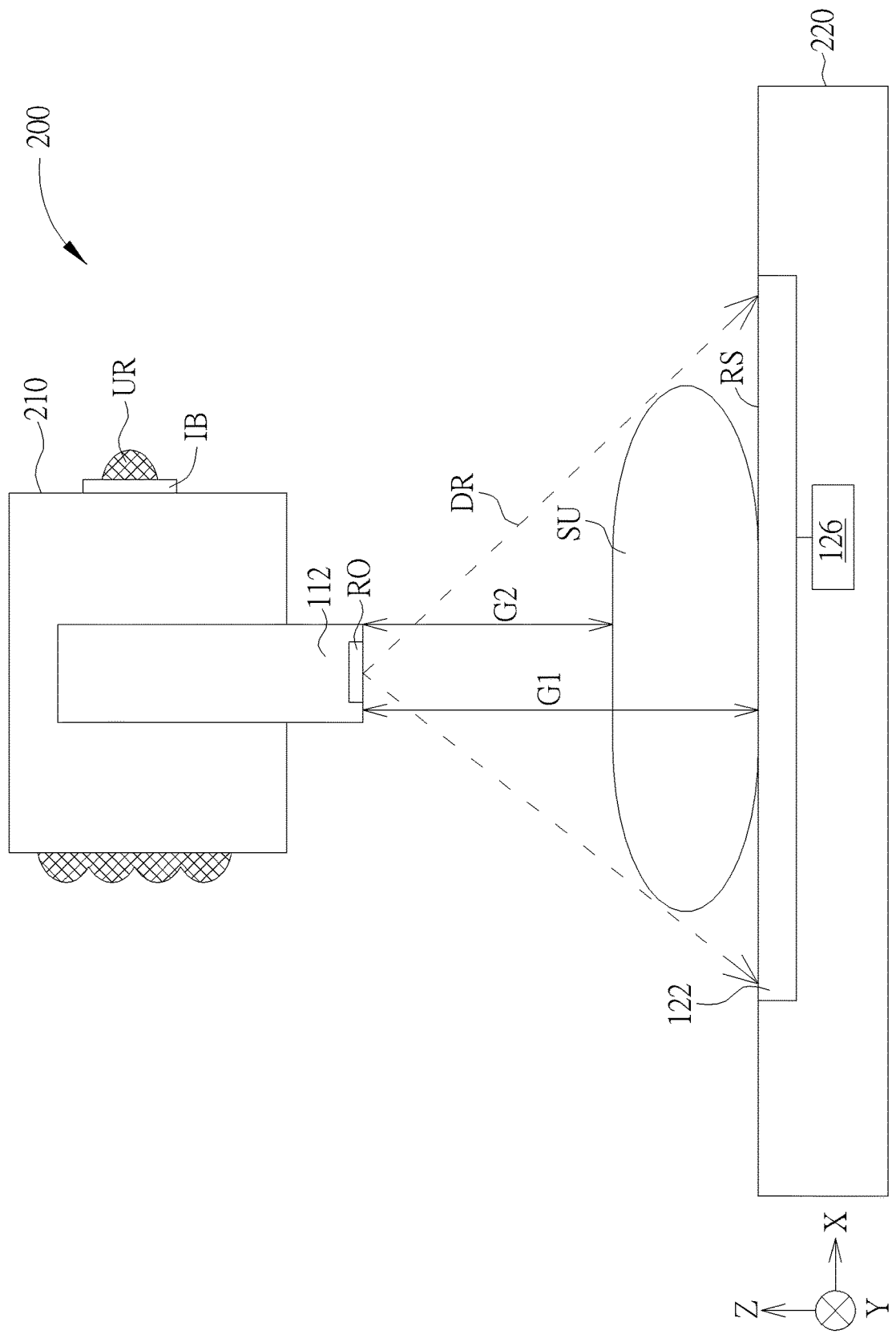
FIG. 10 schematically illustrates a side view of a handheld radiation image detecting system according to a second embodiment of the present invention.
Figure 11:
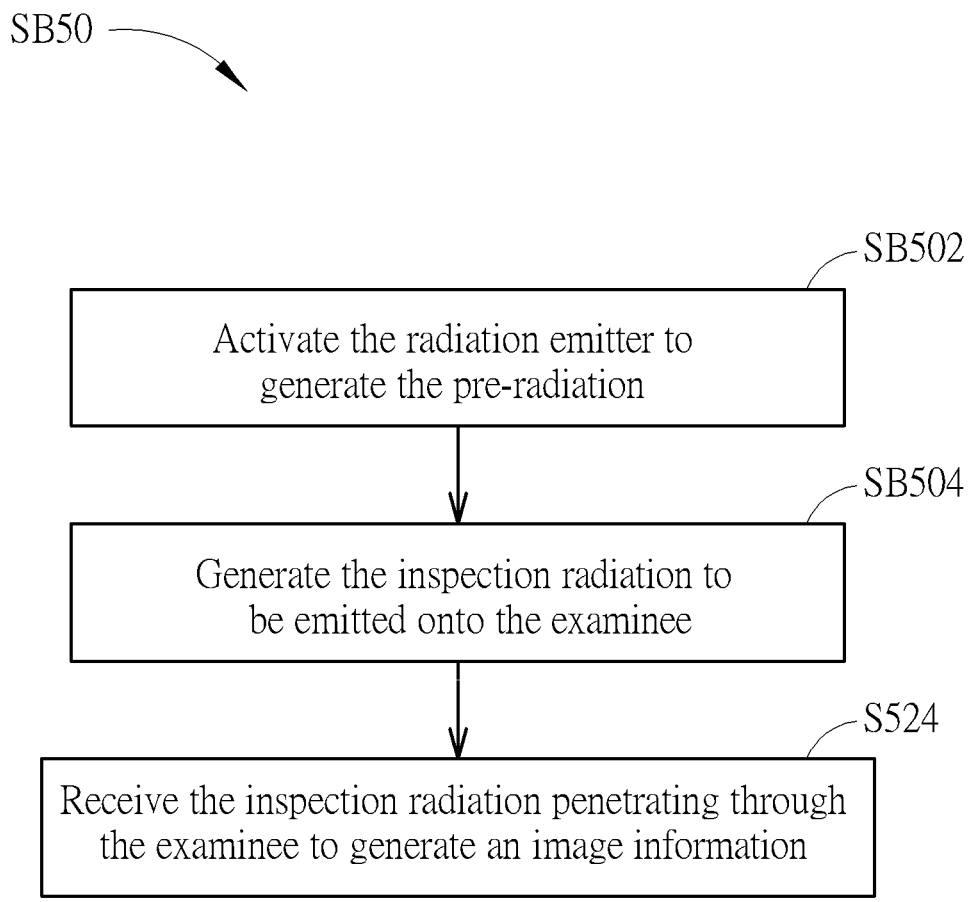
FIG. 11 schematically illustrates a flowchart of an auto-inspection step according to the second embodiment of the present invention.
Figure 12:
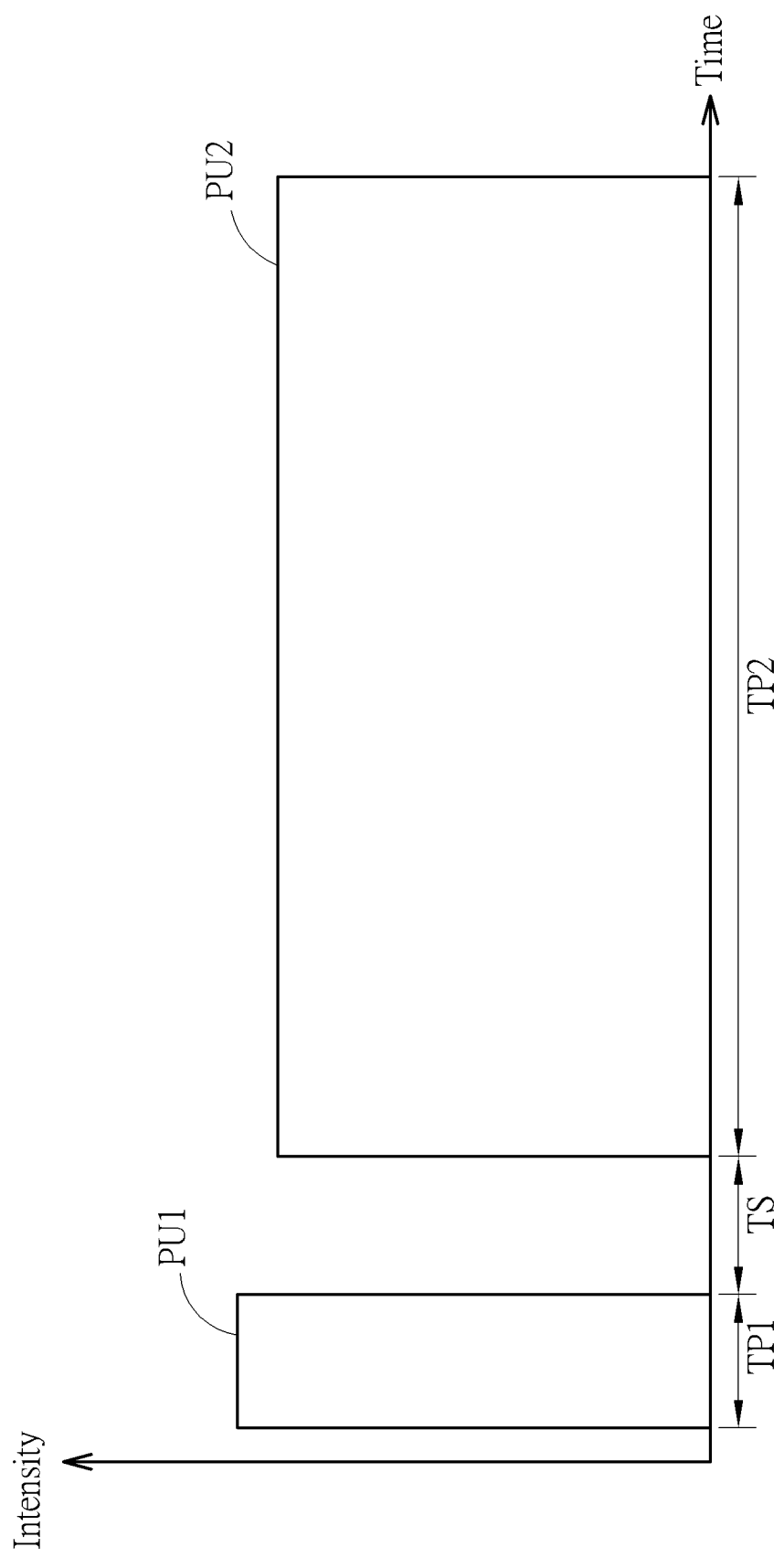
FIG. 12 schematically illustrates a relation between intensity and time of the radiation generated from the radiation emitter according to the second embodiment of the present invention.

FIG. 10 schematically illustrates a side view of a handheld radiation image detecting system according to a second embodiment of the present invention, FIG. 11 schematically illustrates a flowchart of an auto-inspection step according to the second embodiment of the present invention, and FIG. 12 schematically illustrates a relation between intensity and time of the radiation generated from the radiation emitter according to the second embodiment of the present invention. As shown in FIG. 10, as compared with the first embodiment, the handheld radiation image detecting system 200 of this embodiment doesn't include the first transceiver, the second transceiver, the third emitter and the third receiver. As shown in FIG. 11 and FIG. 12, a difference between the operating method provided in this embodiment and the first embodiment is that the radiation emitter 112 in the handheld device 210 further generates a pre-radiation before the inspection radiation is generated in the auto-inspection step SB50 of this embodiment. Specifically, as shown in FIG. 12, a first pulse PU1 in the first time period TP1 represents the pre-radiation, and a second pulse PU2 in the second time period TP2 represents the inspection radiation. The auto-inspection step SB50 of this embodiment can omit the step S502 to the step S522 and perform the step SB502 to directly activate the radiation emitter 112 after pressing the inspection button IB, so as to generate the pre-radiation in the first time period TP1 to activate the sensing device 220, which is to make the sensing device 220 enter a ready state to inspect. The dose of the pre-radiation may be an intensity integral of the first pulse PU1. Then, the step SB504 is performed to generate the inspection radiation DR in the second time period TP2 by the the radiation emitter 112, to be emitted onto the examinee SU. Thereafter, step S524 is performed to receive the inspection radiation DR penetrating through the examinee SU by the radiation image sensor 112, so as to generate an image information.

The dose of the inspection radiation DR may be the intensity integral of the second pulse PU2. It is noted that a time interval TS exists between the first time period TP1 and the second time period TP2, so the radiation image sensor 112 may be prepared in the time interval TS after receiving the pre-radiation. If a front part of the inspection radiation DR is used to activate the radiation image sensor 124, an issue of insufficient dose of inspection radiation DR is easily generated. However, the extra pre-radiation of this embodiment can prevent this issue from happening. In this embodiment, the dose of the pre-radiation is less than the dose of the inspection radiation DR and is as low as possible, so as to inhibit the examinee SU from accumulating over high radiation dose. In another embodiment, the handheld radiation image detecting system 200 using the operating method of the second embodiment may be the same as that of the first embodiment and include the first transceiver, the second transceiver, the third emitter and the third receiver. Also, the step S502 to the step S522 of the first embodiment may be performed before the step SB502 of generating the pre-radiation in the auto-inspection step SB50, so as to further prevent the accident radiation from harming the examinee SU or other persons.

Figure 13:
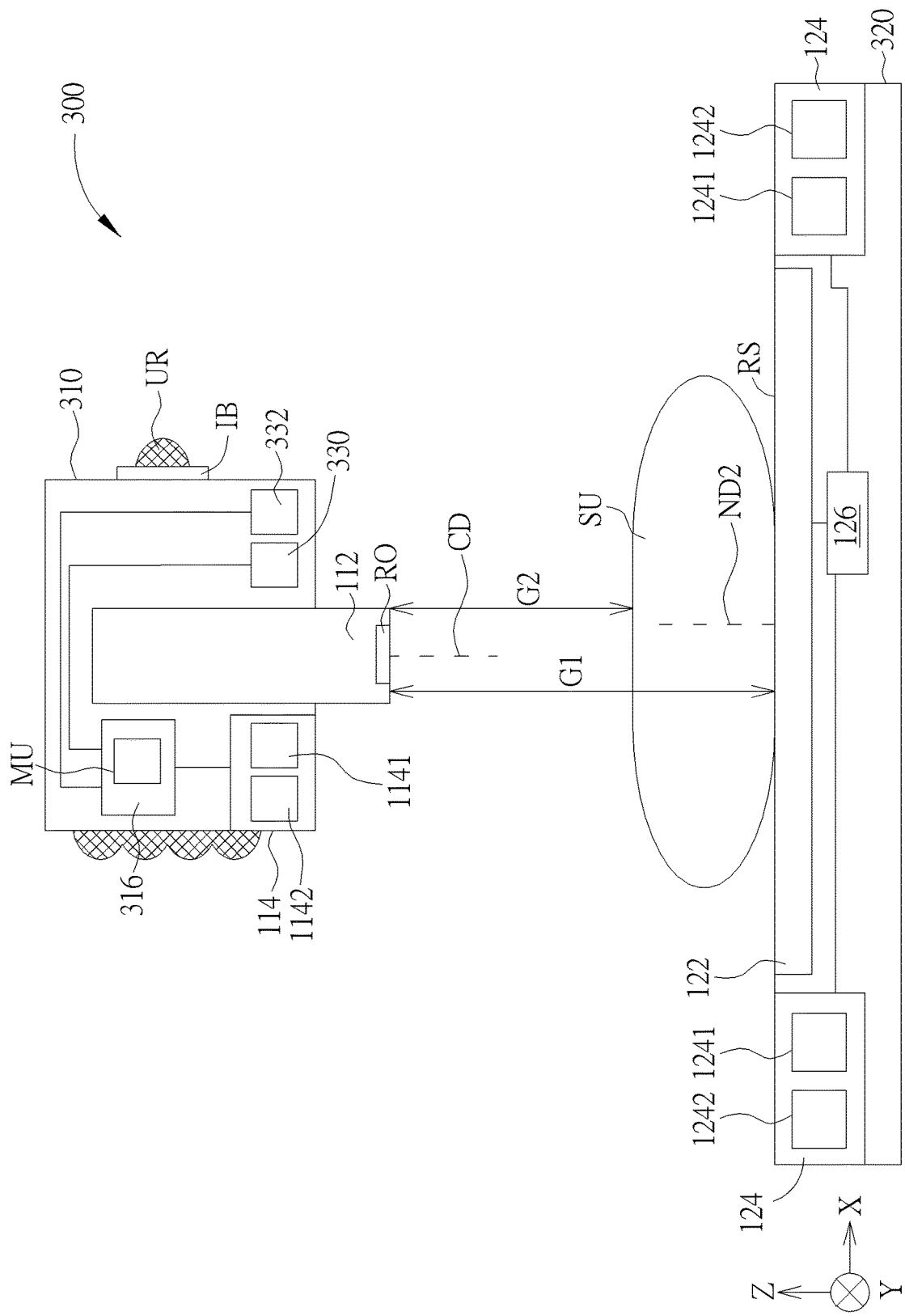
FIG. 13 schematically illustrates a side view of a handheld radiation image detecting system according to a third embodiment of the present invention.
Figure 14:
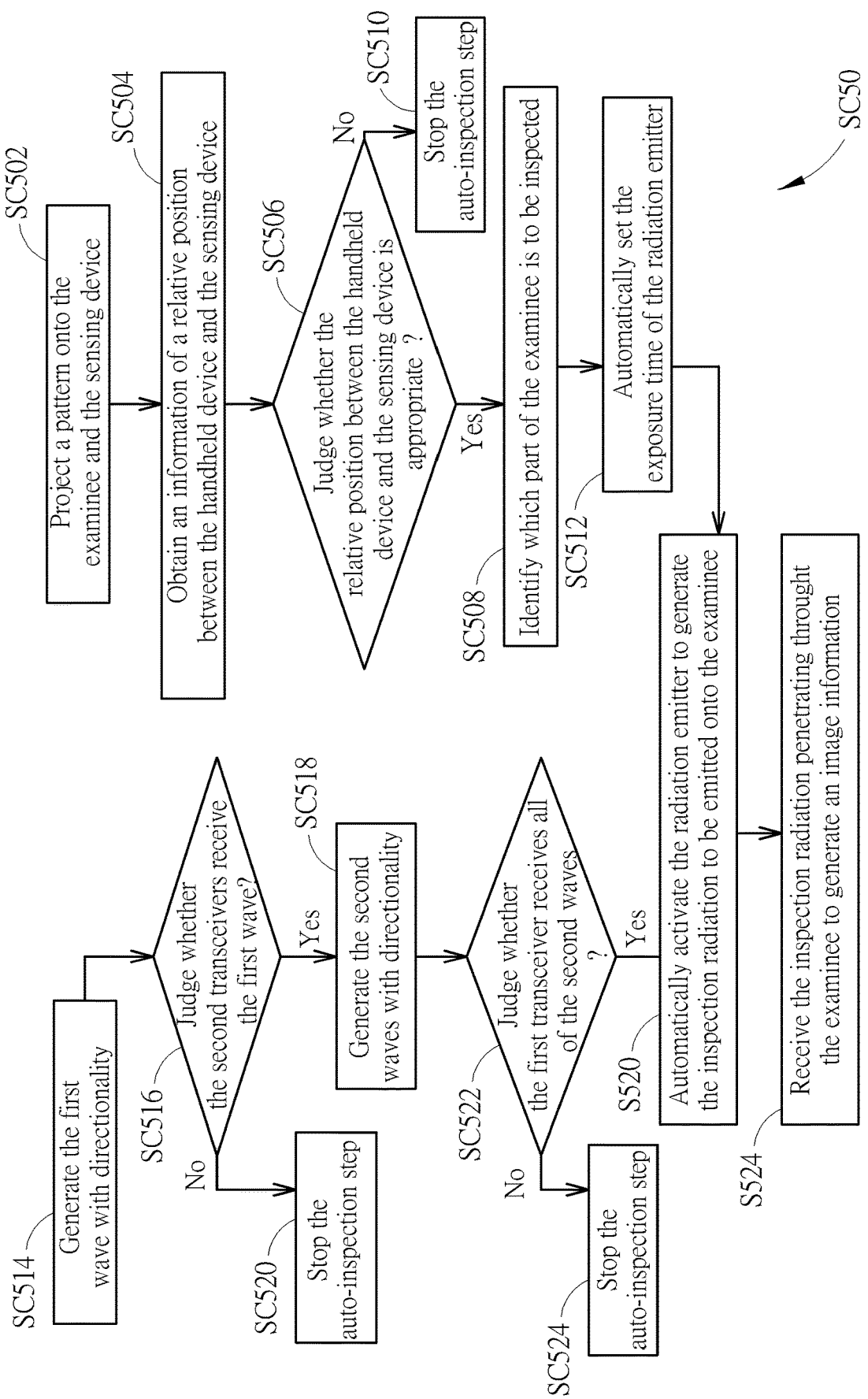
FIG. 14 schematically illustrates a flowchart of an auto-inspection step of the handheld radiation image detecting system according to the third embodiment of the present invention.
Figure 15:
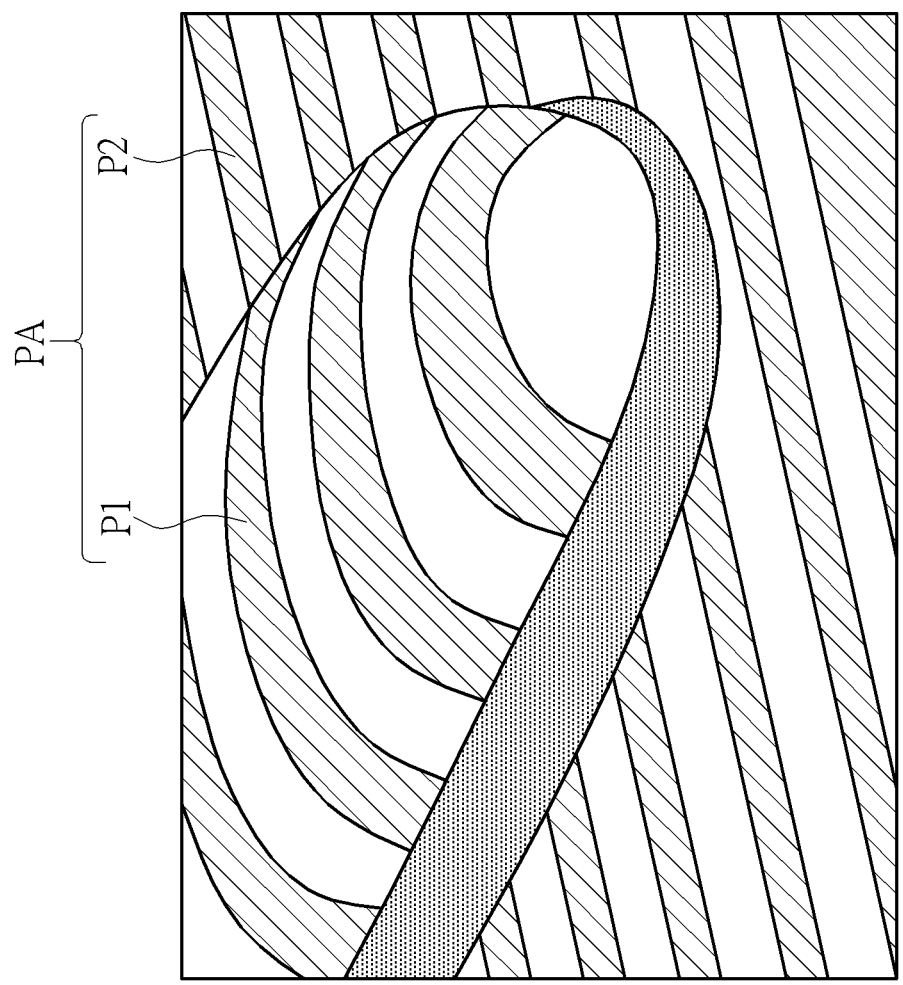
FIG. 15 schematically illustrates a structured light projector projecting a pattern onto the examinee and the sensing device.

FIG. 13 schematically illustrates a side view of a handheld radiation image detecting system according to a third embodiment of the present invention, FIG. 14 schematically illustrates a flowchart of an auto-inspection step of the handheld radiation image detecting system according to the third embodiment of the present invention, and FIG. 15 schematically illustrates a structured light projector projecting a pattern onto the examinee and the sensing device. As shown in FIG. 13, the method for detecting the spacing G1 between the handheld device 310 and the sensing device 320 in the handheld radiation image detecting system 300 of this embodiment is different from the method of the first embodiment. In this embodiment, the handheld radiation image detecting system 300 further includes a structured light projector 330 and an image sensor 332 that are disposed in the handheld device 310, but doesn't include the first timer TI1 and the second timer TI2. The structured light projector 330 is used for projecting a pattern onto the examinee SU and the sensing device 320, and the image sensor 332 is used for detecting the pattern on the examinee SU and the sensing device 320, so as to obtain the spacing G2 between the handheld device 310 and the examinee SU and the spacing G1 between the handheld device 310 and the sensing device 320. In another embodiment, the handheld radiation image detecting system 300 of the third embodiment may not include the first transceiver, the second transceiver, the third emitter and the third receiver, but the present invention is not limited thereto. Also, the first control component 316 of this embodiment may optionally include a memory unit MU for storing a look-up table that records a relation between a part to be inspected and an exposure time of the radiation emitter 112, so the user UR may not need to input the exposure parameter of the radiation emitter 112 before pressing the inspection button IB.

As shown in FIG. 14, a difference between the auto-inspection step SC50 of this embodiment and the first embodiment is that the spacing G1 between the handheld device 310 and the sensing device 320 and the spacing G2 between the handheld 310 and the examinee SU are directly detected by the structured light projector 330 and the image sensor 332 in the auto-inspection step SC50 of this embodiment, and no timer is required to count the propagation time of the wave. Specifically, the auto-inspection step SC50 of this embodiment includes the following steps. As shown in FIG. 13 to FIG. 15, after the step S40 of pressing the inspection button IB, a step SC502 is performed to project a pattern PA onto the examinee SU and the sensing device 320 by the structured light projector 330. Then, the step SC504 is performed to detect a part P1 of the pattern PA projected onto the examinee SU and another part P2 of the pattern PA projected onto the sensing device 320, so that the first control component 116 can obtain an information of a relative position between the handheld device 310 and the sensing device 320.

Figure 16:
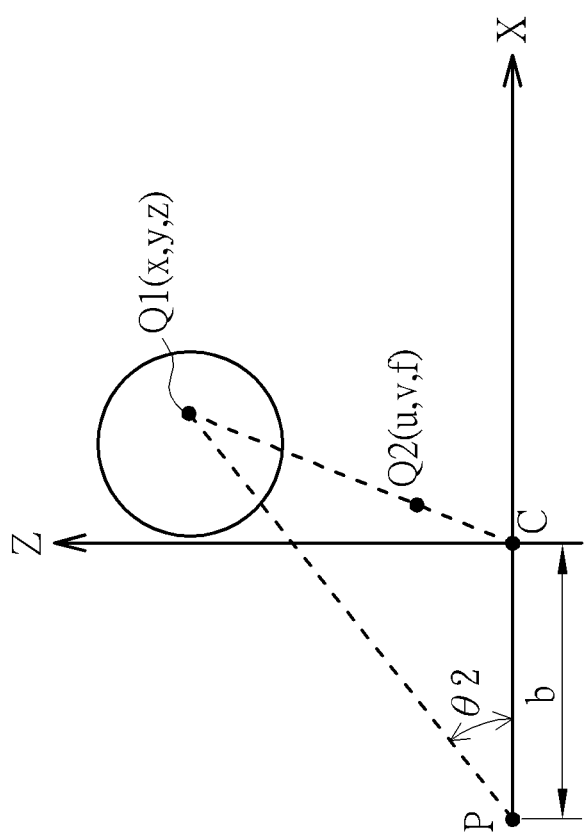
FIG. 16 schematically illustrates a method for measuring a space coordinate points by the structured light projector and the image sensor of this embodiment.

Specifically, refer to FIG. 16, which schematically illustrates a method for measuring a space coordinate points by the structured light projector and the image sensor of this embodiment. As shown in FIG. 16, a point P represents the structured light projector 330, a point C represents the image sensor 332, a point Q1 represents a point on a surface of the object O in the range of the pattern, and a point Q2 represents an imaging position of the point Q1 detected by the image sensor. In a XYZ coordinate system, a coordinate position of the point C is the coordinate origin that is (0, 0, 0), a coordinate position of the point Q is (x, y, z), and a coordinate position of the point Q2 is (u, v, f). Through triangulation, the coordinate position (x, y, z) of the point Q1 may comply with following equation (1).

$$\begin{bmatrix} x \\ y \\ z \end{bmatrix} = \frac{b}{f\cot\theta 2 - u} \begin{bmatrix} u \\ v \\ f \end{bmatrix}, \quad \text{equation (1)}$$

where f is a focal distance of the image sensor 332, b is a spacing between the point P and the point C, and 02 is an angle included between a straight line formed of the point P and the point Q1 and a straight line formed of the point P and the point C. Through the equation (1), the first control component 316 may calculate the information of the relative position between the handheld device 310 and the sensing device 320. For example, the information of the relative position between the handheld device 310 and the sensing device 320 may include at least one of the spacing G1 between the handheld device 310 and the sensing device 320 and the angle between the center axis CD of the radiation emitter 112 and the normal direction ND2 of the sensing device 320. In this embodiment, the first control component 316 may optionally further calculate an information of a relative position between the handheld device 310 and the examinee SU and a thickness of the part of the examinee SU to be inspected, in which the information of the relative position between the handheld 310 and the examinee SU may include the spacing G2 between the handheld device 310 and the examinee SU, but not limited thereto.

The step SC506 is than performed to judge whether the relative position between the handheld device 310 and the sensing device 320 is appropriate according to the information of the relative position between the handheld device 310 and the sensing device 320 by the first control component 316. In this embodiment, when the relative position between the handheld device 310 and the sensing device 320 is appropriate, the step SC508 may be optionally performed. If the relative position between the handheld device 310 and the sensing device 320 is not appropriate, the step SC510 is performed to stop the auto-inspection step SC50.

In the step SC508, the handheld device may identify which part of the examinee SU faced by the radiation outlet RO is to be inspected by the first control component 316 and the image sensor 332. Then, the step S512 is performed to automatically set the exposure time of the radiation emitter 112 according to the identified part, the thickness of the part and the look-up table by the first control component 316. Specifically, the look-up table is prestored in the memory unit MU of the first control component 316, and since the exposure time of the radiation emitter 112 has different values as the part is different or the part has different thickness, the exposure time of the radiation emitter 112 can be confirmed through the thickness of the part and the identified part obtained by the structured light projector 330 and the image sensor 332. The first control component 316 may find the exposure time corresponding to the part in the look-up table according to the information of the part and the thickness of the part and set the exposure time of the radiation source 112 as this exposure time. Thus, the user UR doesn't need to perform the step S10 of inputting the exposure parameter of the radiation emitter 112 before pressing the inspection button IB, and convenience of use for the user UR is raised. The look-up table may be for example the exposure times of the extremities listed in the following table 1, but the present invention is not limited thereto.

TABLE 1

| Extremity | Thickness of part (cm) | | | | | | | |
| --- | --- | --- | --- | --- | --- | --- | --- | --- |
| | 1.5 | 3 | 4.5 | 6 | 7.5 | 9 | 10.5 | 12 |
| | Exposure time (second) | | | | | | | |
| Elbow | 0.04 | 0.08 | 0.12 | 0.16 | 0.20 | 0.24 | 0.42 | 0.48 |
| Anterior-posterior hand | 0.03 | 0.06 | 0.09 | 0.12 | 0.15 | 0.18 | 0.32 | 0.36 |
| Lateral view hand | 0.05 | 0.09 | 0.15 | 0.20 | 0.25 | 0.30 | 0.35 | 0.40 |
| Femur | 0.07 | 0.14 | 0.21 | 0.28 | 0.35 | 0.42 | 0.50 | 0.56 |

In addition, after the step S40 of pressing the inspection button S40, the step SC514 is further performed to generate the first wave SW1 with directionality to be emitted toward the sensing device 320 by the first emitter 1141 of the first transceiver 114. Then, in the step SC516, the second control component 126 may judge whether the second receivers 1242 of the second transceivers 124 receive the first wave SW1, so as to confirm whether the handheld device 310 substantially aims at the sensing device 320. After judging that all of the second receivers 1242 receives the first wave SW1, the step SC518 is performed. If the second control component 126 judges that one of the second receivers 1242 doesn't receive the first eave SW1, the step SC520 is performed to stop the auto-inspection step SC50. The condition for judging the second receivers 1242 receive the first wave SW1 may be the same as the step S504 of the first embodiment, and may be for example that the second receivers 1242 receive the first wave SW1 or the signal values of the first wave SW1 received by the second receivers 1242 are greater than the pre-determined value, but not limited thereto.

In the step SC518, the second emitters 1241 generate the second waves SW2 to be emitted toward the first transceiver 114. After that, the step SC522 is performed to judge whether the first receiver 1142 receives all of the second waves SW2 by the first control component 316, so as to effectively confirm whether the handheld device 310 aims at the sensing device 320 and confirm whether what the handheld device 310 faces is the sensing device 320. When the first control component 316 judges the first receiver 1142 receives all of the second wave SW2, the first control component 316 may confirm the radiation outlet RO of the handheld device 310 faces the sensing device 320 rather than other substrate or device. If the first receiver 1142 doesn't receive one of the second waves SW2, the first control device 116 performs the step SC524 to stop the auto-inspection step SC50. The condition for judging the first receiver 1142 receives all of the second wave SW2 may be for example all of the second waves SW2 are received or the signal values of the received second wave SW2 are greater than the pre-determined value, but not limited thereto. In this embodiment, the second waves SW2 may have different modulation codes, which means the second signals may be different from each other. Also, since the second waves SW2 of this embodiment are generated after the second transceivers 124 receive the first wave SW1, the sensing device 320 doesn't need to continue generating the second wave SW2, so that the sensing device 320 can be in a state of low power consumption, but the present invention is not limited thereto. In another embodiment, the operating method of the handheld radiation image detecting system 300 may omit the steps SC514, SC516 and SC520, and a power supply of the sensing device 320 may be directly turned on by the user UR, so that the second emitters 1241 may continue generating the second wave SW2. For this reason, the handheld device 310 may judge whether the handheld device 310 aims at the sensing device 320 and judge whether the device that the radiation outlet RO faces is the sensing device 320 or not when receiving the second wave SW2. In such situation, the handheld radiation image detecting system 300 may not include the first emitter and the second receiver. It should be noted that since the step SC514 to the step S524 for judging whether the device that the handheld device 310 faces is the sensing device 320 and the step SC502 to the step S512 for detecting the information of the relative position between the handheld device 310 and the sensing device 320 don't influence each other, the step SC514 to the step SC524 and the step SC502 to the step S512 can be performed at the same time, or the step SC514 to the step S524 may be performed before the step SC502 or after the step S512.

After the first control component 316 judges that the condition that the first receiver 1142 receives all of the second waves SW2 and the condition that the setting of the exposure time of the radiation emitter 112 is completed are satisfied, the step S520 is performed to automatically activate the radiation emitter 112 to generate the inspection radiation by the first control component 316, in which the inspection radiation DR is emitted onto the part of the examinee SU to be inspected. Then, the step S524 is performed to receive the inspection radiation DR penetrating through the examinee SU to generate the image information by the radiation image sensor 122. Accordingly, the image information of the examinee SU can be inspected immediately.

In another embodiment, the operating method of the handheld radiation image detecting system 300 may also omit the step SC508 for identifying which part is to be inspected and the step SC512 for automatically setting the exposure time and may perform the step S10 of inputting the exposure parameter of the radiation emitter 112 by user UR. In such situation, when the relative position between the handheld device 310 and the sensing device 320 is appropriate and the first control component 316 judges that the first receiver 1142 receives all of the second waves SW2, the step S520 and the step S524 may be performed.

Figure 17:
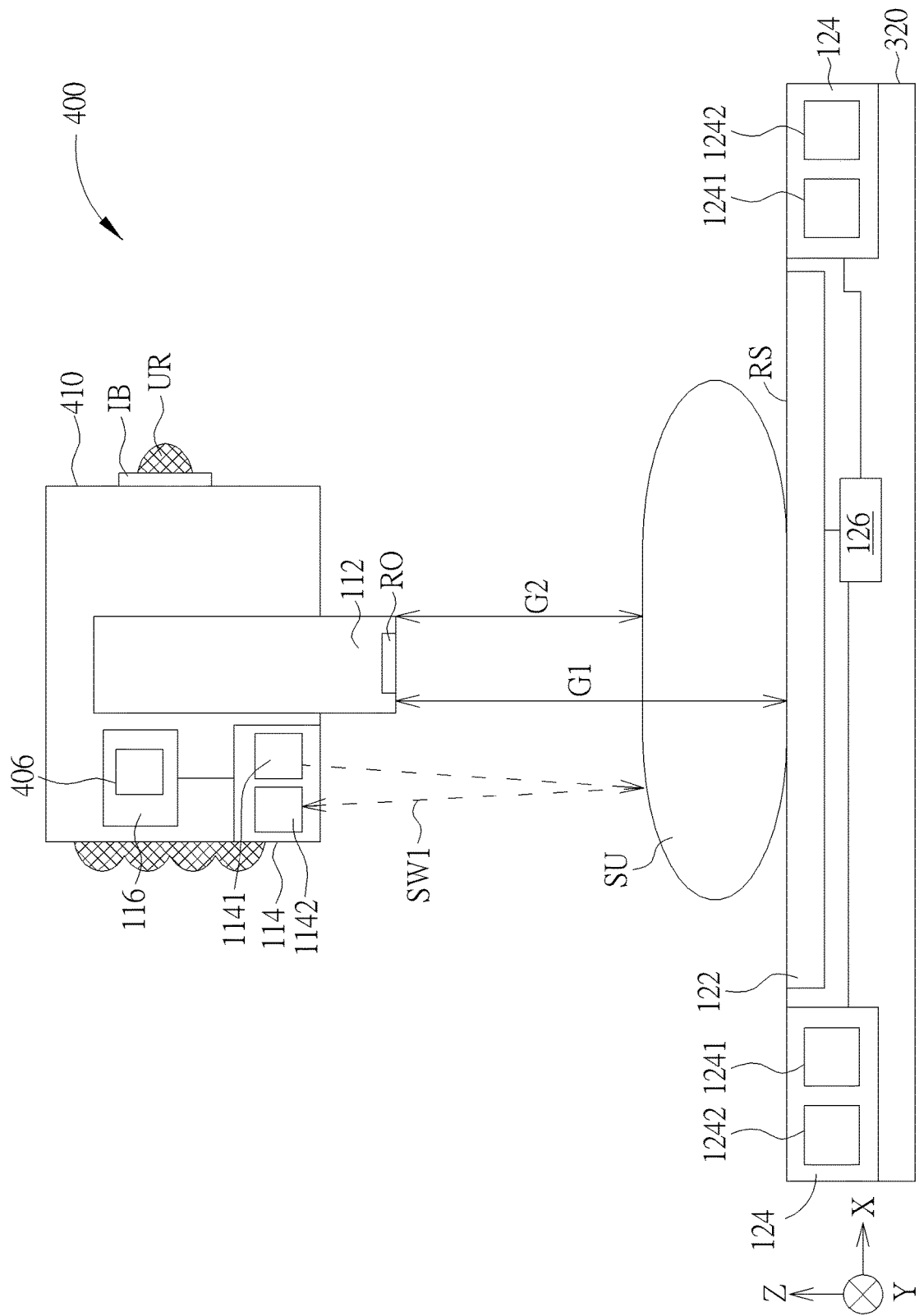
FIG. 17 schematically illustrates a side view of a handheld radiation image detecting system according to a fourth embodiment of the present invention.
Figure 18:
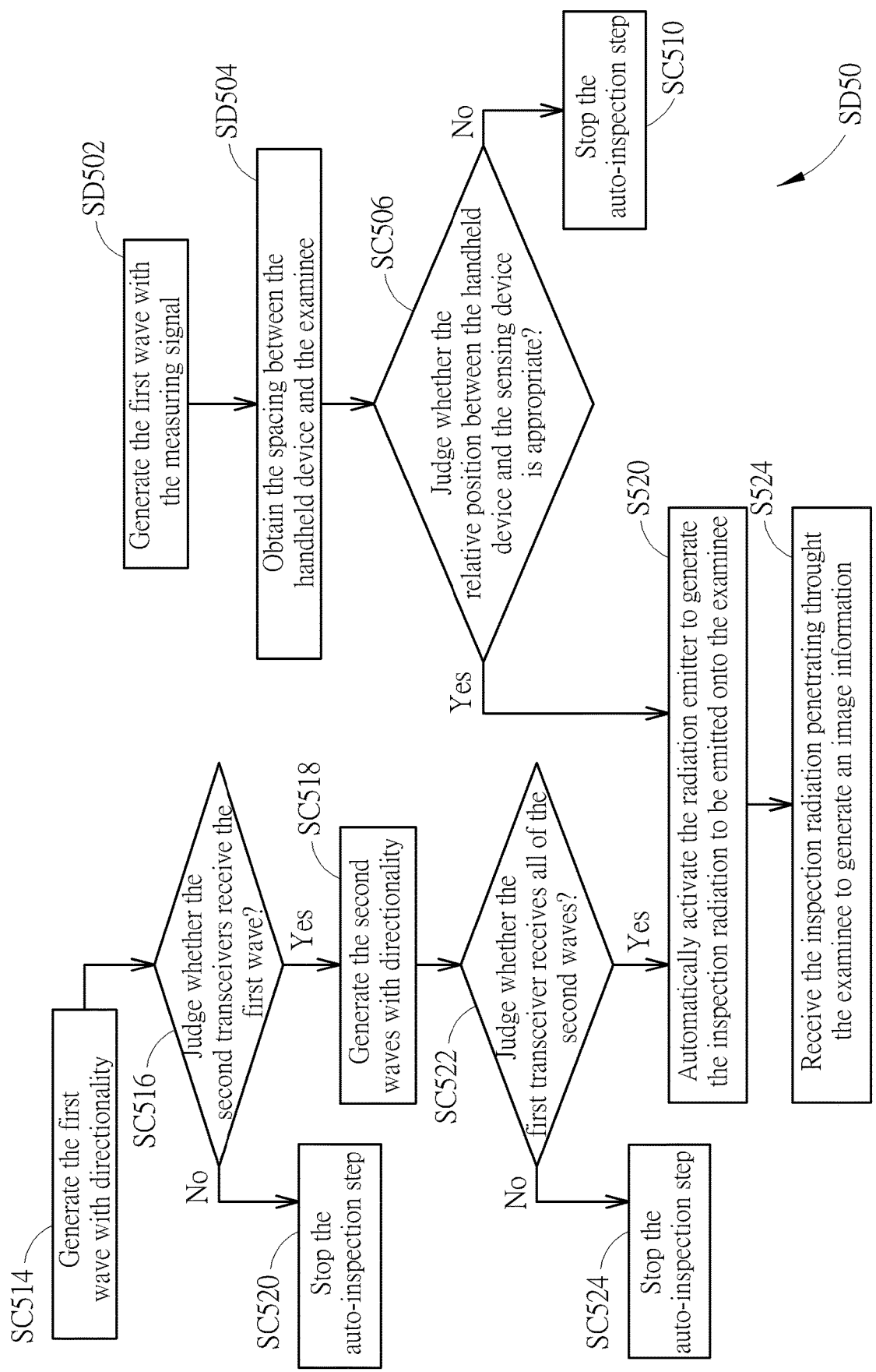
FIG. 18 schematically illustrates a flowchart of an auto-inspection step according to the fourth embodiment of the present invention.

FIG. 17 schematically illustrates a side view of a handheld radiation image detecting system according to a fourth embodiment of the present invention, and FIG. 18 schematically illustrates a flowchart of an auto-inspection step according to the fourth embodiment of the present invention. As shown in FIG. 17, the method for detecting the spacing G1 between the handheld device 410 and the sensing device 420 in the handheld radiation image detecting system 400 of this embodiment is different from the methods in the first embodiment and the third embodiment. As compared with the third embodiment, the first control component 416 of the handheld device 410 of this embodiment further includes a timer 406, and the handheld device 410 doesn't have the structured light projector and the image sensor. The timer 406 can be used for count the propagation time of the first wave with a measuring signal. In another embodiment, the handheld radiation image detecting system 400 of the fourth embodiment may not include the first transceiver, the second transceiver, the third emitter and the third receiver, but not limited thereto.

As shown in FIG. 18, a difference between the auto-inspection step SD50 and the auto-inspection step SC50 is that the auto-inspection step SD50 of this embodiment includes sequentially performing the step SD502 to the step SD504 that replace the step SC502 to the step SC504 of the third embodiment and are used for detecting the spacing G2. In the step SD502, the first emitter 1141 of the first transceiver 114 generates the first wave SW1 with the measuring signal. Then, the first receiver 1142 receives the first wave SW1 reflected by the examinee SU, so as to obtain the spacing G2 between the handheld device 410 and the examinee SU. In this embodiment, the steps in the auto-inspection step SD50 after obtaining the spacing G2 between the handheld device 410 and the examinee SU are the same as the step SC506, the step SC510, the step S520 to the step S524 and the step SC514 to the step SC524, and will not be detailed redundantly. The auto-inspection step SD50 of this embodiment doesn't detect the thickness of the part to be inspected, so the auto-inspection step SD50 doesn't include the step SC508 and the step SC512. In another embodiment, the handheld device 410 may further include a laser emitter and a laser receiver, so that the spacing G2 between the handheld device 410 and the examinee SU and the spacing G1 between the handheld device 410 and the sensing device 420 may be detected by the laser emitter, the laser receiver and the timer based on the technology of time of flight (TOF). In such situation, the auto-inspection step SD50 may detect the thickness of the part to be inspected, so that the auto-inspection step SD50 may include the step SC508 and the step SC512 of the third embodiment.

Figure 19:
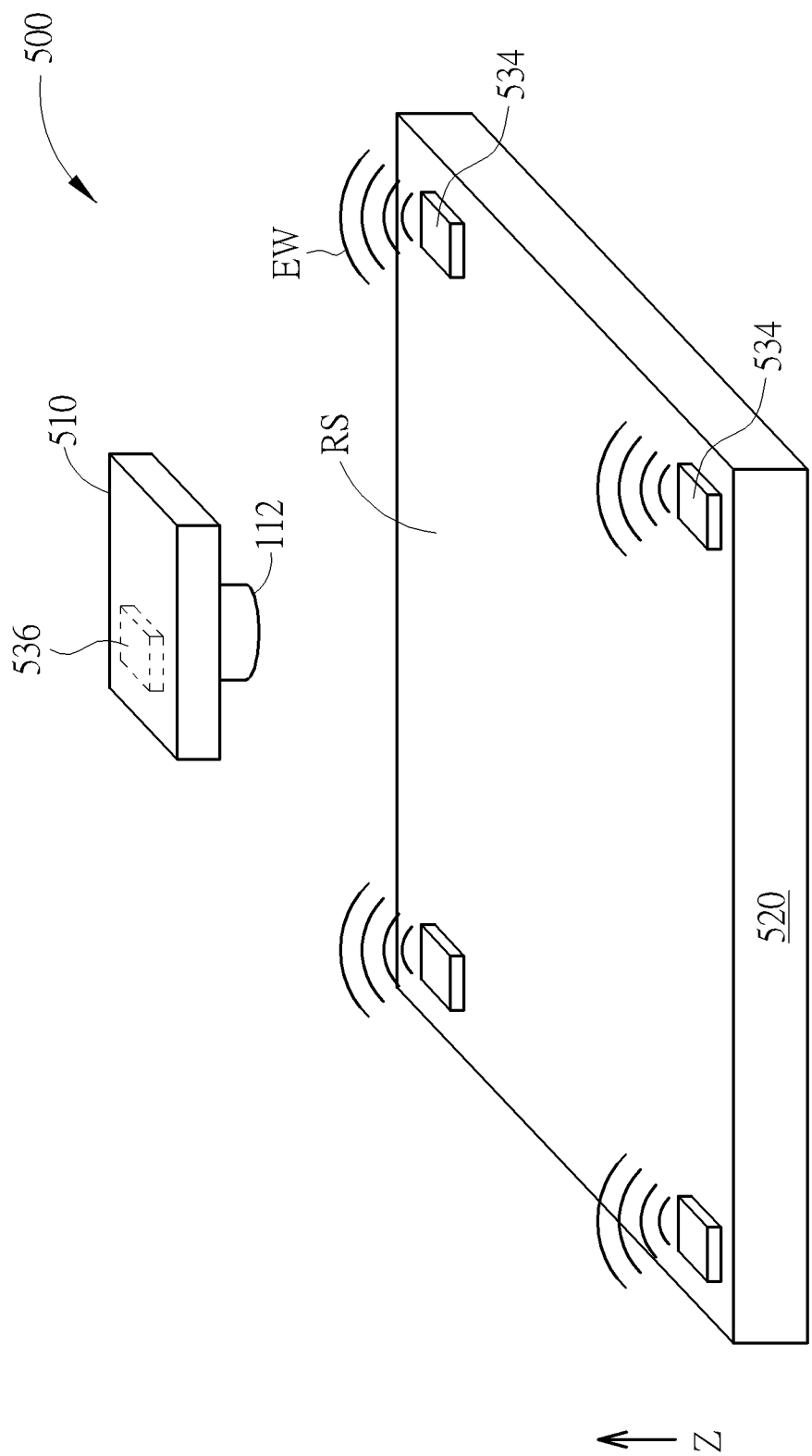
FIG. 19 schematically illustrates a side view of a handheld radiation image detecting system according to a fifth embodiment of the present invention.

FIG. 19 schematically illustrates a side view of a handheld radiation image detecting system according to a fifth embodiment of the present invention. As shown in FIG. 19, as compared with the first embodiment, each second emitter of the sensing device 520 may be an electromagnetic emitter 534 for generating an electromagnetic wave EW, and the first receiver of the handheld device 510 may be an electromagnetic receiver 536 for receiving the electromagnetic waves EW generated from the electromagnetic emitters 534. The electromagnetic emitters 534 are disposed at two corners of the sensing device 520 opposite to each other. A frequency of each electromangnetic wave EW of this embodiment may be in a range from $10^3$ Hz to $10^{16}$ Hz. The electromagnetic waves EW generated from the electromagnetic emitters 534 may have different modulation codes, so that the electromagnetic receiver 536 may accurately receive the signal values of the electromagnetic waves EW generated from the electromagnetic emitters 534. Whether the handheld device 510 having the electromagnetic receiver 536 is disposed right on the center of the sensing device 520 can be judged through the signal values received by the electromagnetic receiver 536. For example, the user can directly move the handheld device 510, and when the signal values of the electromagnetic waves EW received by the electromagnetic receiver 534 are the same, the handheld device 510 can be judged to be disposed right on the center of the sensing device 520. Or, according to the signal values of the electromagnetic waves EW, the spacing between the handheld device 510 and the sensing device 520, the angle included between the center axis of the radiation emitter 112 and the normal direction of the radiation receiving surface RS and a spacing between the center of the handheld device 510 and the center of the sensing device 520 in a top view direction Z.

Figure 20:
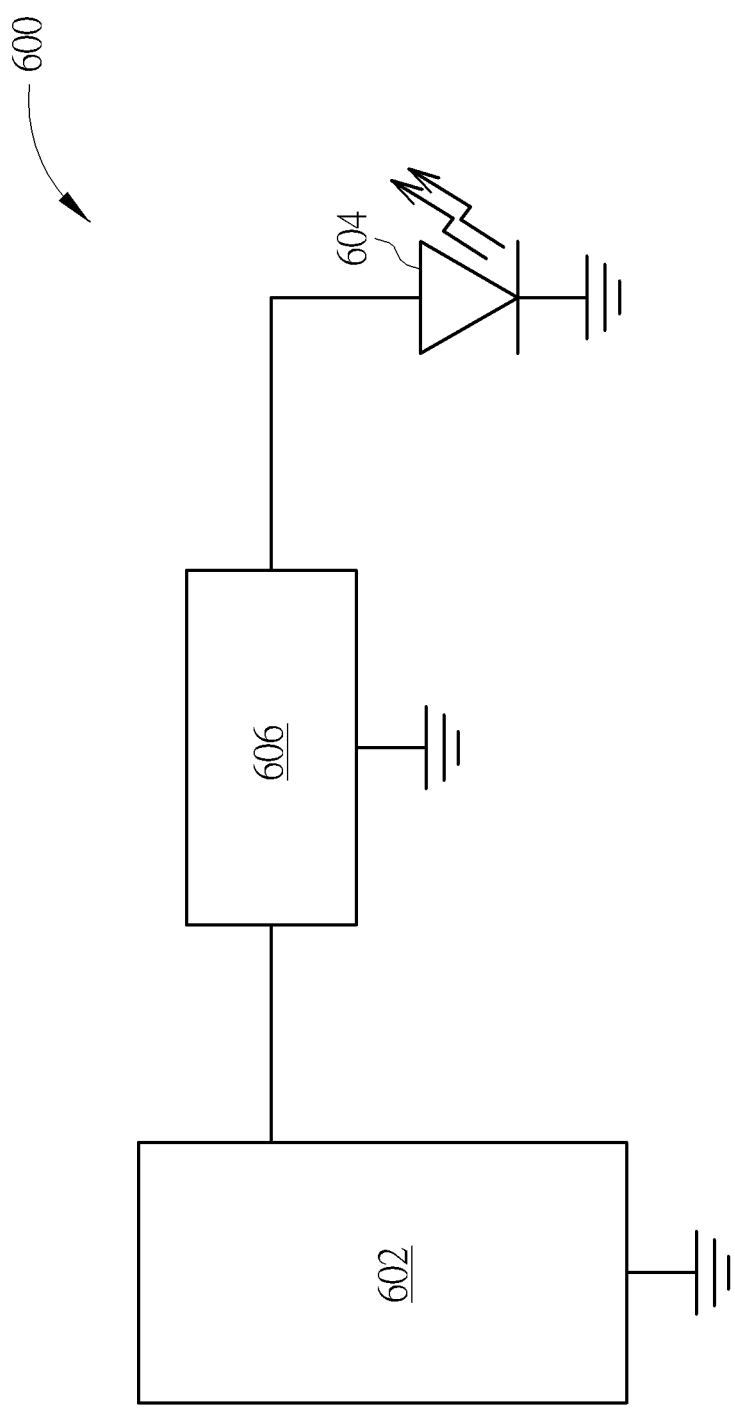
FIG. 20 schematically illustrates a circuit of an emitter according to a sixth embodiment of the present invention.

FIG. 20 schematically illustrates a circuit of an emitter according to a sixth embodiment of the present invention. As shown in FIG. 20, the emitter 600 provided in this embodiment includes a driving circuit 602, a light-emitting element 604 and an over-current protection circuit 606. The over-current protection circuit 606 is coupled between the driving circuit 602 and the light-emitting element 604, the driving circuit 602 and the over-current protection circuit 606 are separately coupled to a ground end, and the light-emitting element 604 is coupled between the over-current protection circuit 606 and the ground end. For example, the over-current protection circuit 606 may be a resettable fuse, but not limited thereto. It is noted that since the light-emitting element 604 may generate the infrared light that human eyes cannot see, through coupling the over-current protection circuit 606 between the driving circuit 602 and the light-emitting element 604, the current provided to the light-emitting element 604 can be confined to limit brightness of the infrared light generated from the light-emitting element 604. Accordingly, the eyes of the user or examinee can be protected from being harmed by the infrared light. The emitter 600 of this embodiment may be adapted to the first emitter or the second emitter of the handheld radiation image detecting system in any one of the above-mentioned embodiments.

Figure 21:
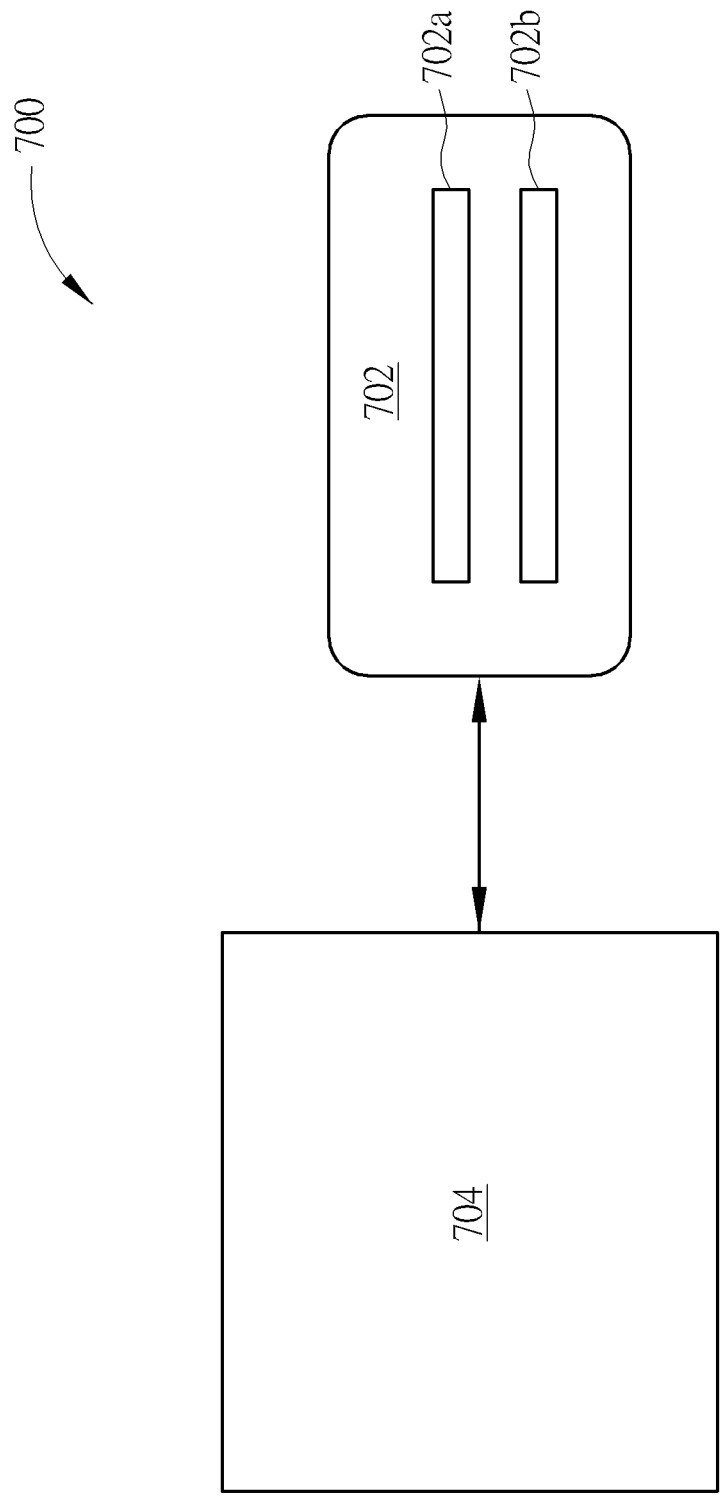
FIG. 21 is a schematic block diagram of a handheld radiation image detecting system according to a seventh embodiment of the present invention.

FIG. 21 is a schematic block diagram of a handheld radiation image detecting system according to a seventh embodiment of the present invention. As shown in FIG. 21, the handheld radiation image detecting system 700 of this embodiment may include an embedded system 702 coupled to the radiation image sensor 704. For example, the embedded system 702 may be a field-programmable gate array (FPGA) system and be disposed in the sensing device or coupled to the sensing device. In this embodiment, the radiation image sensor 704 and the sensing device may be the radiation image sensor and sensing device of any one of the above-mentioned embodiments respectively. The embedded system. 702 may include a calibration unit 702a and a medical image format conversion processing unit 702b, in which the calibration unit 702a is used for adjusting sensitivity of the radiation image sensor 704 with respect to the radiation, the medical image format conversion processing unit 702b is used for converting a data information sensed by the radiation image sensor 704 into a format of a medical image, so that medical personnel can inspect. In this embodiment, the calibration unit 702a and the medical image format conversion processing unit 702b are integrated into one embedded system 702, so that cost, volume, and power consumption of the handheld radiation image detecting system 700 can be reduced.

As the mentioned above, in the operating method of the handheld radiation image detecting system, the step of the first emitter emitting the first wave toward the second receiver, the step of the third emitter emitting the third wave toward the third receiver and the step of second emitter transmitting the second wave back to the first receiver are performed in a time period less than 500 ms, so as to quickly achieve the auto-inspection step, or the spacing detecting step performed through the structured light projector and the image sensor or the first emitter, the first receiver and the timer in combination with the step of generating the second wave by the second emitter are performed to judge whether the shift between the handheld device and the sensing device in the XY plane and the spacing in the top view direction are appropriate. Accordingly, the issue that the radiation emitter generates the radiation at incorrect position or incorrect angle can be avoided. For this reason, the examinee or the user is prevented from receiving unnecessary dose of radiation, so as to reduce harm of the radiation to the examinee and the user. Also, through the wireless communication method of the first transceiver and the second transceiver, the handheld device and the sensing device may not require extra wired line to connect each other, and thus, the convenience of use of the handheld radiation image detecting system can be improved.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A handheld radiation image detecting system for inspecting an examinee, comprising:
    a handheld device comprising a radiation emitter and a first transceiver, wherein the first transceiver is coupled to the radiation emitter, the first transceiver comprises a first emitter and a first receiver, and the first emitter is used for generating a first wave with directionality; and
    a sensing device comprising a radiation image sensor and at least one second transceiver, wherein the at least one second transceiver comprises a second emitter and a second receiver, the second receiver is used for receiving the first wave, the second emitter is used for generating a second wave with directionality, and the first receiver is used for receiving the second wave.

2. The handheld radiation image detecting system according to claim 1, wherein the first wave and the second wave comprise an ultrasonic wave, an infrared light or a visible light.

3. The handheld radiation image detecting system according to claim 1, wherein the at least one second transceiver comprises four second transceivers, and the second transceivers are disposed at four corners of the sensing device respectively.

4. The handheld radiation image detecting system according to claim 1, wherein the handheld device further comprises a third emitter and a first timer, the third emitter is used for generating a third wave, the sensing device further comprises a third receiver and a second timer, the third receiver is used for receiving the third wave, the first timer and the second timer are used for counting a propagation time of the third wave, and a propagation speed of the third wave is less than a propagation speed of the first wave and less than a propagation speed of the second wave.

5. The handheld radiation image detecting system according to claim 1, wherein the third wave is an ultrasonic wave, and the first wave and the second wave comprise an infrared light or a visible light.

6. The handheld radiation image detecting system according to claim 1, wherein the handheld device further comprises a structured light projector and an image sensor, the structured light projector projects a pattern onto the examinee and the sensing device, and the image sensor is used for detecting a part of the pattern projected onto the examinee and another part of the pattern projected onto the sensing device to obtain a spacing between the handheld device and the examinee and another spacing between the handheld device and the sensing device.

7. The handheld radiation image detecting system according to claim 1, wherein the handheld device further comprises a timer, the first emitter is used for generating the first wave with a measuring signal, the first receiver is used for receiving the first wave, and the timer is used for counting a propagation time of the first wave.

8. An operation method of a handheld radiation image detecting system for inspecting an examinee, wherein the handheld radiation image detecting system comprises a handheld device and a sensing device, the handheld device comprises a radiation emitter, a first transceiver, an emitter, and a first timer, the sensing device comprises a radiation image sensor, at least one second transceiver, a receiver, and a second timer, and the operation method comprises:
    pressing an inspection button of the handheld device by a user;
    performing an auto-inspection step to judge whether a relative position between the handheld device and the sensing device is appropriate, wherein the auto-inspection step comprises:
        generating a first wave with directionality by the first transceiver, and obtaining a first time point of generating the first wave by the timer;
        when the second transceiver receives the first wave, obtaining another first time point by the second timer;
        generating a third wave by the emitter, and obtaining a second time point by the first timer, wherein the third wave is emitted toward the sensing device;
        when the receiver receives the third wave, obtaining a propagation time of the third wave and a third time point of receiving the third wave by the second timer, and generating a second wave with directionality by the second transceiver, wherein a propagation speed of the third wave is less than a propagation speed of the first wave and less than a propagation speed of the second wave;
        when the first transceiver receives the second wave, obtaining another third time point by the first timer; and
        calculating a spacing between the handheld device and the sensing device, and judging whether the relative position between the handheld device and the sensing device is appropriate;
    when the relative position between the handheld device and the sensing device is appropriate, automatically activating the radiation emitter to generate an inspection radiation to be irradiated onto the examinee; and
    receiving the inspection radiation penetrating through the examinee by the radiation image sensor, so as to generate an image information.

9. The operation method of the handheld radiation image detecting system according to claim 8, wherein the first time point of generating the first wave is identical to the second time point of generating the third wave, and the propagation time of the third wave is a time difference between the third time point and the another first time point.

10. The operation method of the handheld radiation image detecting system according to claim 8, wherein the second time point of generating the third wave is later than the first time point of generating the first wave, a first time difference exists between the first time point and the second time point, the operation method further comprises obtaining another second time point of starting to count when the third wave is generated by the second timer, and the first time difference exists between the another second time point and the another first time point.

11. The operation method of the handheld radiation image detecting system according to claim 10, wherein the propagation time of the third wave is a second time difference between the third time point and the another second time point.

12. The operation method of the handheld radiation image detecting system according to claim 8, wherein the at least one second transceiver comprises four second transceivers disposed at four corners of the sensing device respectively, generating the second wave comprises generating four second waves respectively by the second transceivers, and obtaining the another third time point further comprises judging whether the first transceiver receives the second waves.

13. An operation method of a handheld radiation image detecting system for inspecting an examinee, wherein the handheld radiation image detecting system comprises a handheld device and a sensing device, the handheld device comprises a radiation emitter and a first transceiver, the sensing device comprises a radiation image sensor and at least one second transceiver, and the operation method comprises:
   pressing an inspection button of the handheld device by a user;
   performing an auto-inspection step to judge whether a relative position between the handheld device and the sensing device is appropriate, wherein the auto-inspection step comprises:
      generating a wave by the second transceiver, wherein the wave has directionality; and
      when the first transceiver receives the wave, judging the handheld device facing the sensing device;
   when the relative position between the handheld device and the sensing device is appropriate, automatically activating the radiation emitter and generating an inspection radiation to be irradiated onto the examinee; and
   receiving the inspection radiation penetrating through the examinee by the radiation image sensor, so as to generate an image information.

14. The operation method of the handheld radiation image detecting system according to claim 13, wherein generating the wave comprises:
   generating another wave with directionality by the first transceiver; and
   when the second transceiver receives the another wave, generating the wave by the second transceiver.

15. The operation method of the handheld radiation image detecting system according to claim 13, wherein generating the wave comprises turning on a power supply of the sensing device.

16. The operation method of the handheld radiation image detecting system according to claim 13, wherein the handheld device further comprises a structured light projector and an image sensor, and the auto-inspection step further comprises:
   projecting a pattern onto the examinee and the sensing device by the structured light projector;
   detecting a part of the pattern projected onto the examinee and another part of the pattern projected onto the sensing device by the image sensor, so as to obtain an information of a relative position between the handheld device and the sensing device; and
   judging whether the relative position between the handheld device and the sensing device is appropriate according to the information of the relative position between the handheld device and the sensing device.

17. The operation method of the handheld radiation image detecting system according to claim 16, wherein the auto-inspection step further comprises:
   identifying a part of the examinee to be inspected by the image sensor, wherein obtaining the information of the relative position between the handheld device and the sensing device comprises obtaining a thickness of the part of the examinee to be inspected; and
   setting an exposure time of the radiation emitter by a control component according to a look-up table, the part of the examinee and the thickness of the part of the examinee.

18. The operation method of the handheld radiation image detecting system according to claim 13, wherein the auto-inspection step further comprises:
   generating another wave with a measuring signal by the first transceiver; and
   receiving the another wave reflected from the sensing device by the first transceiver, so as to obtain a spacing between the handheld device and the examinee.

* * * * *